United States Patent [19]

Scherkenbeck et al.

[11] Patent Number: 5,777,075

[45] Date of Patent: *Jul. 7, 1998

[54] OCTACYCLODEPSIPEPTIDES HAVING AN ENDOPARASITICIDAL ACTION

[75] Inventors: Jürgen Scherkenbeck; Peter Jeschke, both of Leverkusen; Hans-Georg Lerchen, Köln; Hermann Hagemann, Leverkusen; Achim Harder, Köln; Norbert Mencke, Leverkusen; Andrew Plant, Odenthal, all of Germany

[73] Assignee: Bayer Aktiengesellschaft, Leverkusen, Germany

[*] Notice: The term of this patent shall not extend beyond the expiration date of Pat. No. 5,525,591.

[21] Appl. No.: 510,084

[22] Filed: Aug. 1, 1995

Related U.S. Application Data

[62] Division of Ser. No. 246,029, May 19, 1994.

[30] Foreign Application Priority Data

May 26, 1993 [DE] Germany .................. 43 17 457.4

[51] Int. Cl.⁶ .................. C07K 11/00; A61K 38/15
[52] U.S. Cl. .................. 530/330; 530/328; 530/323; 514/16; 514/18
[58] Field of Search .................. 530/330, 328, 530/323; 514/16, 18

[56] References Cited

U.S. PATENT DOCUMENTS

| | | | |
|---|---|---|---|
| 5,116,815 | 5/1992 | Takagi et al. | 514/11 |
| 5,525,591 | 6/1996 | Scherkenbeck et al. | 514/8 |

FOREIGN PATENT DOCUMENTS

| | | |
|---|---|---|
| 0382173 | 8/1990 | European Pat. Off. . |
| 0503538 | 9/1992 | European Pat. Off. . |
| 503538 | 9/1992 | European Pat. Off. . |

OTHER PUBLICATIONS

Isogi et al. "Bassianolide: Synthesis of its Analogs and NMR Studies". Peptide Chemistry. pp. 165–170. 1979.
Ivanov et al. Peptides. Proc. European Symp., vol. 6, pp. 337–350, 1963.
Peptide Chemistry 1978. Protein Research Foudation; "Bassianolide: Syntheses or its Analogs and NMR Studies". A. Isogai et al., pp. 165–170.
The Journal of Antibiotics, May 1992; pp. 692–697; "A New Anthelmintic Cyclodepsipeptide, PF1022A", T. Sasaki et al.
Chemical Abstract, vol. 79, No. 3, Jul. 23, 1973, Columbus, Ohio, US; Abstract No. 19074.
Chemical Abstract, vol. 66, No. 7, Feb. 13, 1967, Columbus, Ohio, US; Abstract No. 29078.
Chemische Berichte, Bd. 101, Nr. 5, 1968, Weinheim DE.
Tetrahedron Letters, Nr. 46, 1977, Oxford GB
Chemical Abstract, vol. 119, No. 21, Nov. 22, 1993, Columbus, Ohio, US; Abstract No. 224429.

*Primary Examiner*—Cecilia J. Tsang
*Assistant Examiner*—Anish Gupta
*Attorney, Agent, or Firm*—Sprung Kramer Schaefer & Briscoe

[57] ABSTRACT

The present invention relates to the use of open-chain octadepsipeptides of the general formula:

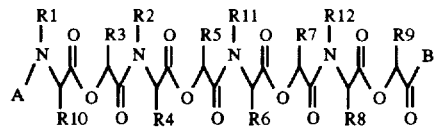

wherein the R variables have been defined in the specification.

5 Claims, No Drawings

OCTACYCLODEPSIPEPTIDES HAVING AN ENDOPARASITICIDAL ACTION

This is a division of application Ser. No. 08/246,029, filed on May 19, 1994 now pending.

The present invention relates to new octacyclodepsipeptides and to a plurality of processes for their preparation, and to their use as endoparasiticides.

European Published Specification 0 382 173 discloses a cyclic depsipeptide with the designation PF 1022. The compound possesses an anthelmintic action. At low application rates, however, the activity in some cases leaves something to be desired.

The present invention relates, then, to:
1. Compounds of the general formula (I)

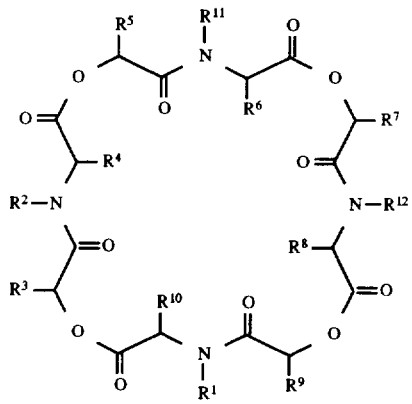

in which $R^1$, $R^2$, $R^{11}$ and $R^{12}$ represent the same or different radicals selected from the group of $C_{1-8}$-alkyl, $C_{1-8}$-halogenoalkyl, $C_{3-6}$-cycloalkyl, aralkyl or aryl.

$R^3$, $R^5$, $R^7$, $R^9$, represent the same or different radicals selected from the group of hydrogen or straight-chain $C_{1-5}$-alkyl or branched $C_{4-7}$-alkyl which may optionally be substituted by hydroxyl, $C_{1-4}$-alkoxy,

imidazolyl, indolyl, guanidino, —SH or $C_{1-4}$-alkylthio, and furthermore represents aryl, aralkyl or heteroarylmethyl which may be substituted by halogen, hydroxyl, $C_{1-4}$-alkyl, $C_{1-4}$-alkoxy, nitro or a —$NR^{13}R^{14}$ group in which $R^{13}$ and $R^{14}$ independently from each other represent hydrogen or alkyl or together with the adjoining nitrogen atom forms a 5, 6 or 7-membered ring which is optionally interrupted by O, S or N and which is optionally $C_{1-4}$-alkyl substituted.

$R^4$, $R^6$, $R^8$, $R^{10}$ represent the same or different radicals selected from the group of hydrogen, straight-chain $C_{1-5}$-alkyl and represents isopropyl, sec.-butyl, t-butyl, $C_{2-6}$-alkenyl, $C_{3-7}$-cycloalkyl, which may optionally be substituted by hydroxyl, $C_{1-4}$-alkoxy, carboxyl, carboxamide, imidazolyl, indolyl, guanidino, SH or $C_{1-4}$-alkylthio and represent aryl, aralkyl or heteroarylmethyl which may be substituted by halogen, hydroxyl, $C_{1-4}$-alkyl, $C_{1-4}$-alkoxy, and stereoisomers thereof.

2. Process for the preparation of the compounds of the formula (I)

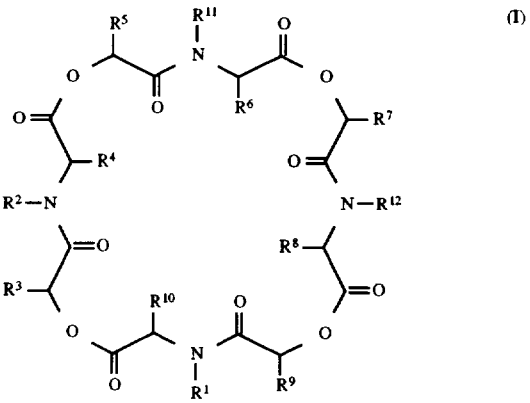

in which $R^1$, $R^2$, $R^{11}$ and $R^{12}$ represent the same or different radicals selected from the group of $C_{1-8}$-alkyl, $C_{1-8}$-halogenoalkyl, $C_{3-6}$-cycloalkyl, aralkyl or aryl.

$R^3$ represents hydrogen or straight-chain $C_{1-5}$-alkyl which may optionally be substituted by hydroxyl, $C_{1-4}$-alkoxy,

imidazolyl, indolyl, guanidino, —SH or $C_{1-4}$-alkylthio, and represents isopropyl or sec.-butyl and furthermore represents aryl, aralkyl or heteroarylmethyl which may be substituted by halogen, hydroxyl, $C_{1-4}$-alkyl, $C_{1-4}$alkoxy, nitro or a —$NR^{13}R^{14}$ group in which $R^{13}$ and $R^{14}$ independently from each other represent hydrogen or alkyl or together with the adjoining nitrogen atom forms a 5, 6 or 7-membered ring which is optionally interrupted by O, S or N and which is optionally $C_{1-4}$-alkyl substituted.

$R^4$ to $R^{10}$ represent the same or different radicals selected from the group of hydrogen, straight-chain $C_{1-5}$-alkyl which may optionally be substituted by hydroxyl, $C_{1-4}$-alkoxy, carboxyl, carboxamide, imidazolyl, indolyl, guanidino, SH or $C_{1-4}$-alkylthio, and represent aryl, aralkyl or heteroarylmethyl which may be substituted by halogen, hydroxyl, $C_{1-4}$-alkyl, $C_{1-4}$-alkoxy, nitro or a —$NR^{13}R^{14}$ group in which $R^{13}$ and $R^{14}$ independently from each other represent hydrogen or alkyl or together with the adjoining nitrogen atom forms a 5, 6 or 7-membered ring which is optionally interrupted by O, S or N and which is optionally $C_{1-4}$-alkyl substituted, characterized in that open-chain octadepsipeptides of the formula (II)

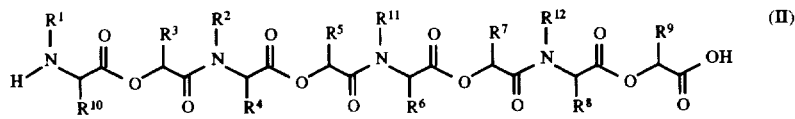

in which
R$^1$ to R$^{12}$ have the meaning given above are cyclized in the presence of a diluent and in the presence of a coupling reagent;

3. Open-chain octadepsipeptides of the formula (II)

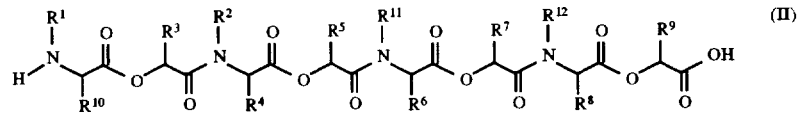

in which R$^1$, R$^2$, R$^{11}$ and R$^{12}$ represent the same or different radicals selected from the group of C$_{1-8}$-alkyl, C$_{1-8}$-halogenoalkyl, C$_{3-6}$-cycloalkyl, aralkyl, alkyl, R$^3$, R$^5$, R$^7$, R$^9$ represent "the same or different radicals selected from the group of" hydrogen or straight-chain C$_{1-5}$-alkyl or branched C$_{4-7}$-alkyl which may optionally be substituted by hydroxyl, C$_{1-4}$-alkoxy,

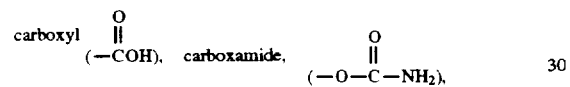

imidazolyl, indolyl, guanidino, —SH or C$_{1-4}$-alkylthio and furthermore represents aryl, aralkyl or heteroarylmethyl which may be substituted by halogen, hydroxyl, C$_{1-4}$-alkyl, C$_{1-4}$-alkoxy, nitro or a —NR$^{13}$R$^{14}$ group in which R$^{13}$ and R$^{14}$ independently from each other represent hydrogen or alkyl or together with the adjoining nitrogen atom forms a 5, 6 or 7-membered ring which is optionally interrupted by O, S or N and which is optionally C$_{1-4}$-alkyl substituted, R$^4$, R$^6$, R$^8$, R$^{10}$ represent the same or different radicals selected from the group of hydrogen, straight-chain C$_{1-5}$-alkyl and represents isopropyl, sec.-butyl, t-butyl, C$_{2-6}$-alkenyl, C$_{3-7}$-cycloakyl, which may optionally be substituted by hydroxyl, C$_{1-4}$-alkoxy, carboxyl, carboxamide, imidazolyl, indolyl, guanidino, SH or C$_{1-4}$-alkylthio, and represent aryl, aralkyl or heteroarylmethyl which may be substituted by halogen, hydroxyl, C$_{1-4}$-alkyl, C$_{1-4}$-alkoxy, and stereoisomers thereof.

4. Process for the preparation of the open-chain octadepsipeptides of the formula (II)

in which
R$^1$, R$^2$, R$^{11}$ and R$^{12}$ represent the same or different radicals selected from the group of C$_{1-8}$-alkyl, C$_{1-8}$-halogenoalkyl, C$_{3-6}$-cycloalkyl, aralkyl, aryl, R$^3$, R$^5$, R$^7$, R$^9$ represent the same or different radicals selected from the group of hydrogen or straight-chain C$_{1-5}$-alkyl or branched C$_{4-7}$-alkyl which may optionally be substituted by hydroxyl, C$_{1-4}$-alkoxy, carboxyl

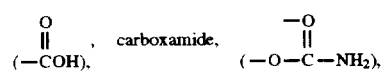

imidazolyl, indolyl, guanidino, —SH

C$_{1-4}$-alkylthio and furthermore represents aryl, aralkyl or heteroarylmethyl which may be substituted by halogen, hydroxyl, C$_{1-4}$-alkyl, C$_{1-4}$-alkoxy, nitro or a —NR$^{13}$R$^{14}$ group in which R$^{13}$ and R$^{14}$ independently from each other represent hydrogen or alkyl or together with the adjoining nitrogen atom forms a 5, 6 or 7-membered ring which is optionally interrupted by O, S or N and which is optionally C$_{1-4}$-alkyl substituted.

R$^4$, R$^6$, R$^8$, R$^{10}$ represent the same or different radicals selected from the group of hydrogen, straight-chain C$_{1-5}$-alkyl and represents isopropyl, sec.-butyl, t-butyl, C$_{2-6}$-alkenyl, C$_{3-7}$-cycloakyl, which may optionally be substituted by hydroxyl, C$_{1-4}$-alkoxy, carboxyl, carboxamide, imidazolyl, indolyl, guanidino, SH or C$_{1-4}$-alkylthio, and represent aryl, aralkyl or heteroaryl-methyl which may be substituted by halogen, hydroxyl, C$_{1-4}$-alkyl, C$_{1-4}$-alkoxy, characterized in that compounds of the formula (III)

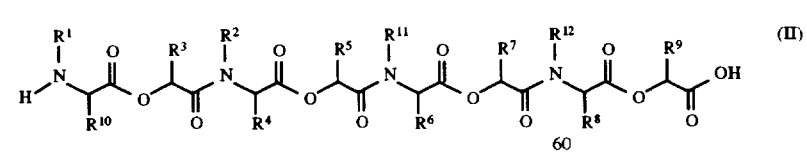

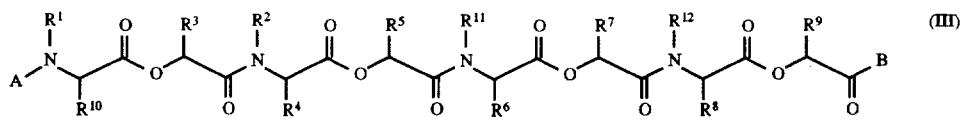

in which

A represents benzyl and

B represents OH and $R^1$ to $R^{12}$ possess the meaning given above are subjected in the presence of a diluent and a catalyst to hydrogenolysis.

5. Compounds of the formula (III)

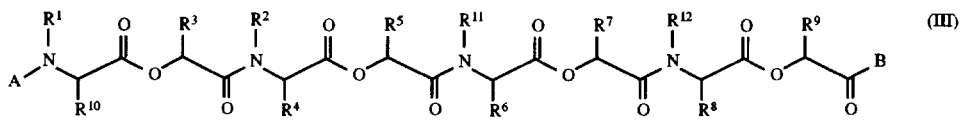

in which

A represents benzyl and

B represents OH and $R^1$, $R^2$, $R^{11}$ and $R^{12}$ represent the same or different radicals selected from the group of $C_{1-8}$-alkyl, $C_{1-8}$-halogenoalkyl, $C_{3-6}$-cycloalkyl, aralkyl, aryl, $R^3$, $R^5$, $R^7$, $R^9$ represent the same or different radicals selected from the group of hydrogen or straight-chain $C_{1-5}$-alkyl or branched $C_{4-7}$-alkyl which may optionally be substituted by hydroxyl, $C_{1-4}$-alkoxy,

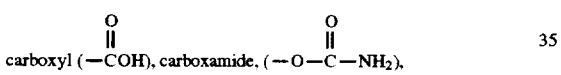

imidazolyl, indolyl, guanidino, —SH $C_{1-4}$-alkylthio and furthermore represents aryl, aralkyl or heteroarylmethyl which may be substituted by halogen, hydroxyl, $C_{1-4}$-alkyl, $C_{1-4}$-alkoxy, nitro or a -$NR^{13}R^{14}$ group in which $R^{13}$ and $R^{14}$ independently from each other represent hydrogen or alkyl or together with the adjoining nitrogen atom forms a 5, 6 or 7-membered ring which is optionally interrupted by O, S or N and which is optionally $C_{1-4}$-alkyl substituted.

$R^4$, $R^6$, $R^8$, $R^{10}$ represent the same or different radicals selected from the group o- hydrogen, straight-chain $C_{1-5}$-alkyl and represents isopropyl, sec.-butyl, t-butyl, $C_{2-6}$-alkenyl, $C_{3-7}$-cycloakyl, which may optionally be substituted by hydroxyl, $C_{1-4}$-alkoxy, carboxly, carboxamide, imidazolyl, indolyl, guanidino, SH or $C_{1-4}$-alkylthio, and represent aryl, aralkyl or heteroarylmethyl which may be substituted by halogen, hydroxyl, $C_{1-4}$-alkyl, $C_{1-4}$-alkoxy.

6. Process for the preparation of the compounds of the formula (III)

$C_{1-5}$-alkyl or branched $C_{4-7}$-alkyl which may optionally be substituted by hydroxyl, $C_{1-4}$-alkoxy,

imidazolyl, indolyl, guanidino, —SH $C_{1-4}$-alkylthio and further more represents aryl, aralkyl or heteroarylmethyl which may be substituted by halogen, hydroxyl, $C_{1-4}$-alkyl, $C_{1-4}$-alkoxy, nitro or a —$NR^{13}R^{14}$ group in which $R^{13}$ and $R^4$ independently from each other represent hydrogen or alkyl or together with the adjoining nitrogen atom forms a 5, 6 or 7-membered ring which is optionally interrupted by O, S or N and which is optionally $C_{1-4}$-alkyl substituted.

$R^4$, $R^6$, $R^8$, $R^{10}$ represent the same or different radicals selected from the group of hydrogen, straight-chain $C_{1-5}$-alkyl and represents isopropyl, sec.-butyl, t-butyl, $C_{2-6}$-alkenyl, $C_{3-7}$-cycloakyl, which may optionally be substituted by hydroxyl, $C_{1-4}$-alkoxy, carboxyl, carboxamide, imidazolyl, indolyl, guanidino, SH or $C_{1-4}$-alkylthio, and represent aryl, aralkyl or heteroarylmethyl which may be substituted by halogen, hydroxyl, $C_{1-4}$-alkyl, $C_{1-4}$-alkoxy, characterized in that compounds of the formula (IV)

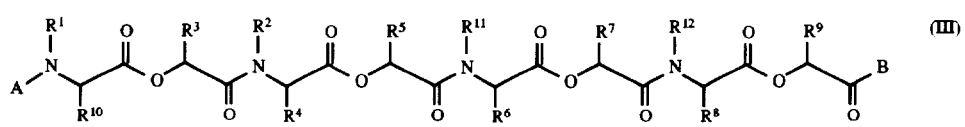

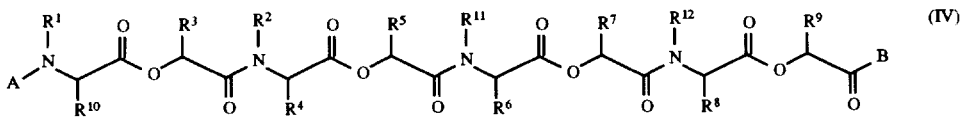

in which

A represents benzyl and

B represents tert.-butoxy, and $R^1$, $R^2$, $R^{11}$ and $R^{12}$ represent the same or different radicals selected from the group of $C_{1-8}$-alkyl, $C_{1-8}$-halogenoalkyl, $C_{3-6}$-cycloalkyl, aralkyl, alkyl, $R^3$, $R^5$, $R^7$, $R^9$ represent the same or different radicals selected from the group of hydrogen or straight-chain $C_{1-5}$-alkyl or branched $C_{4-7}$-alkyl which may optionally be substituted by hydroxyl, $C_{1-4}$-alkoxy,

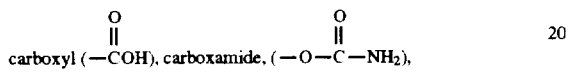

carboxyl (—COH), carboxamide, (—O—C—NH$_2$), imidazolyl, indolyl, guanido, —SH $C_{1-4}$-alkylthio and furthermore represents aryl, aralkyl or heteroarylmethyl which may be substituted by halogen, hydroxyl, $C_{1-4}$-alkyl, $C_{1-4}$-alkoxy, nitro or a —NR$^{13}$R$^{14}$ group in which $R^{13}$ and $R^{14}$ independently from each other represent hydrogen or alkyl or together with the adjoining nitrogen atom forms a 5, 6 or 7-membered ring which is optionally interrupted by O, S or N and which is optionally $C_{1-4}$-alkyl substituted, $R^4$, $R^6$, $R^8$, $R^{10}$ represent the same or different radicals selected from the group of hydrogen, straight-chain $C_{1-5}$-alkyl and represents isopropyl, sec.-butyl, t-butyl, $C_{2-6}$-alkenyl, $C_{3-7}$-cycloakyl, which may optionally be substituted by hydroxyl, $C_{1-4}$-alkoxy, carboxyl, carboxamide, imidazolyl, indolyl, guanidino, SH or $C_{1-4}$-alkylthio, and represent aryl, aralkyl or heteroarylmethyl which may be substituted by halogen, hydroxyl, $C_{1-4}$-alkyl, $C_{1-4}$-alkoxy.

7. Process for the preparation of the compounds of the formula (IV)

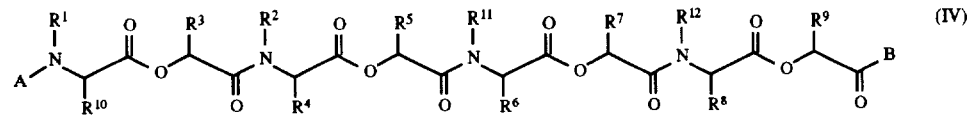

in which

A represents benzyl and

B represents tert.-butoxy, and $R^1$, $R^2$, $R^{11}$ and $R^{12}$ represent the same or different radicals selected from the group of, $C_{1-8}$-alkyl, $C_{1-8}$-halogenoalkyl, $C_{3-6}$-cycloalkyl, aralkyl, aryl, $R^3$, $R^5$, $R^7$, $R^9$ represent the same or different radicals selected from the group of hydrogen or straight-chain $C_{1-5}$-alkyl or branched $C_{4-7}$-alkyl which may optionally be substituted by hydroxyl, $C_{1-4}$-alkoxy,

carboxyl (—COH), carboxamide, (—O—C—NH$_2$), imidazolyl, indolyl, guanidino, —SH $C_{1-4}$-alkylthio and furthermore represents aryl, aralkyl or heteroarylmethyl which may be substituted by halogen,
hydroxyl, $C_{1-4}$-alkyl, $C_{1-4}$-alkoxy, nitro or a -NR$^{13}$R$^4$ group in which $R^{13}$ and $R^{14}$ independently from each other represent hydrogen or alkyl or together with the adjoining nitrogen atom forms a 5, 6 or 7-membered ring which is optionally interrupted by O, S or N and which is optionally $C_{1-4}$-alkyl substituted, $R^4$, $R^6$, $R^8$, $R^{10}$ represent the same or different radicals selected from the group of hydrogen, straight-chain $C_{1-5}$-alkyl and represents isopropyl, sec.-butyl, t-butyl, $C_{2-6}$-alkenyl, $C_{3-7}$-cycloakyl, which may optionally be substituted by hydroxyl, $C_{1-4}$-alkoxy, carboxyl, carboxamide, imidazolyl, indolyl, guanidino, SH or $C_{1-4}$-alkylthio, and represent-aryl, aralkyl or heteroarylmethyl which may be substituted by halogen, hydroxyl, $C_{1-4}$-alkyl, $C_4$-alkoxy.

and stereoisomers thereof, characterized in that tetradepsipeptides of the formula (V)

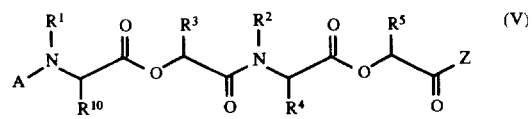

in which

A represents benzyl and

Z represents OH and $R^1$, $R^2$, $R^3$, $R^4$, $R^5$ and $R^{10}$ have the meaning given above.

and tetradepsipeptides of the formula (VI)

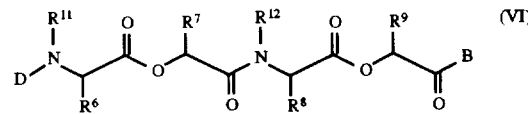

in which

D represents hydrogen and

B represents tert.-butoxy, and $R^6$, $R^7$, $R^8$, $R^9$, $R^{11}$ and $R^{12}$ have the meaning given above.

are condensed in the presence of a diluent and a coupling reagent.

8. Tetradepsipeptides of the formula (V)

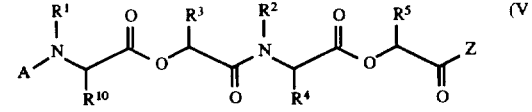

in which

A represents benzyl and

Z represents OH and $R^1$, $R^2$ represent the same or different radicals selected from the group of $C_{1-8}$-alkyl, $C_{1-8}$-halogenoalkyl, $C_{3-6}$-cycloalkyl, aralkyl, aryl,

9

$R^3$, $R^5$ represent the same or different radicals selected from the group of hydrogen or straight-chain $C_{1-5}$-alkyl or branched $C_{4-7}$-alkyl which may optionally be hydroxy, $C_{1-4}$-alkoxy,

carboxyl (—COH), carboxamide, (—O—C—NH$_2$), imidazolyl, indolyl, guanidino, —SH or $C_{1-4}$-alkylthio and furthermore represent aryl or aralkyl or heteroarylmethyl which may be substituted by halogen, hydroxyl, $C_{1-4}$-alkyl, $C_{1-4}$-alkoxy, nitro or a —NR$^{13}$R$^{14}$ group in which R$^{13}$ and R$^{14}$ independently from each other represent hydrogen or alkyl or together with the adjoining nitrogen atom forms a 5, 6 or 7-membered ring which is optionally interrupted by O, S or N and which is optionally $C_{1-4}$-alkyl substituted, $R^4$, $R^{10}$ represents the same or different radicals selected from the group of hydrogen or straight-chain branched $C_{1-5}$-alkyl and represents $C_{2-6}$-alkenyl or $C_{3-7}$-cycloalkyl which may optionally be substituted by hydroxyl, $C_{1-4}$-alkoxy, carboxyl, carboxamide, imidazolyl, indolyl, guanidino, SH or $C_{1-4}$-alkylthio, and represent aryl or aralkyl which may be substituted by halogen, hydroxyl, $C_{1-4}$-alkyl, $C_{1-4}$-alkoxy.

9. Tetradepsipeptides of the formula (VI)

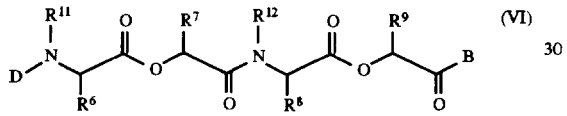

in which

D represents hydrogen and

B represents tert.-butoxy, and $R^{11}$, $R^{12}$ represent the same or different radicals selected from the group of $C_{1-8}$-alkyl, $C_{1-8}$-halogenoalkyl, $C_{3-6}$-cycloalkyl, aralkyl, aryl, $R^7$, $R^9$ represent the same or different radicals selected from the group of hydrogen or straight-chain $C_{1-5}$-alkyl or branched $C_{4-7}$-alkyl which may optionally be substitut ed by hydroxyl, $C_{1-4}$-alkoxy,

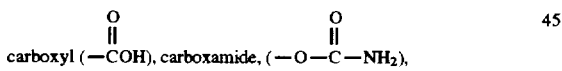
carboxyl (—COH), carboxamide, (—O—C—NH$_2$), imidazolyl, indolyl, guanidino, —SH or $C_{1-4}$-alkylthio and furthermore represent aryl or aralkyl or heteroarylmethyl which may be substituted by halogen, hydroxyl, $C_{1-4}$-alkyl, $C_{1-4}$-alkoxy, nitro or a —NR$^{13}$R$^{14}$ group in which R$^{13}$ and R$^{14}$ independently from each other represent hydrogen or alkyl or together with the adjoining nitrogen atom forms a 5, 6 or 7-membered ring which is optionally interrupted by O, S or N and which is optionally $C_{1-4}$-alkyl substituted, $R^6$, $R^8$ represent the same or different radicals selected from the group of hydrogen,straight-chain or branched $C_{1-5}$-alkyl and represents $C_{2-6}$-alkenyl, $C_{3-7}$-cycloalkyl which may optionally be substituted by hydroxyl, $C_{1-4}$-alkoxy, carboxyl, carboxamide, imidazolyl, indolyl, guanidino, SH or $C_{1-4}$-alkylthio, and represent aryl or aralkyl which may be substituted by halogen, hydroxyl, $C_{1-4}$-alkyl, $C_{1-4}$-alkoxy.

10. Process for the preparation of the tetradepsipeptides of the formula (V)

10

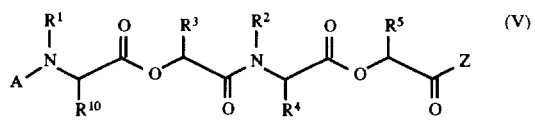

in which

A represents benzyl and

Z represents OH and $R^1$, $R^2$ represent the same or different radicals selected from the group of $C_{1-8}$-alkyl, $C_{1-8}$-halogenoalkyl, $C_{3-6}$-cycloalkyl, aralkyl, aryl, $R^3$, $R^5$ represent the same or different radicals selected from the group of hydrogen or straight-chain $C_{1-5}$-alkyl or branched $C_{4-7}$-alkyl which may optionally be substituted by hydroxyl, $C_{1-4}$-alkoxy,

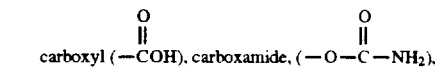
carboxyl (—COH), carboxamide, (—O—C—NH$_2$), imidazolyl, indolyl, guanidino, —SH, or $C_{1-4}$-alkylthio, and furthermore represents aryl, aralkyl, or heteroarylmethyl which may be substituted by halogen, hydroxyl, $C_{1-4}$-alkyl, $C_{1-4}$-alkoxy, nitro or a —NR$^{13}$R$^{14}$ group in which R$^{13}$ and R$^{14}$ independently from each other represent hydrogen or alkyl or together with the adjoining nitrogen atom forms a 5, 6 or 7-membered ring which is optionally interrupted by O, S or N and which is optionally $C_{1-4}$-alkyl substituted, $R^4$, $R^{10}$ represent the same or different radicals selected from the group of hydrogen,straight-chain or branched $C_{1-5}$-alkyl and represents $C_{2-6}$-alkenyl or $C_{3-7}$-cycloalkyl which may optionally be substituted by hydroxyl, $C_{1-4}$-alkoxy, carboxyl, carboxamide, imidazolyl, indolyl, guanidino, SH or $C_{1-4}$-alkylthio, and represent aryl or aralkyl which may be substituted by halogen, hydroxyl, $C_{1-4}$-alkyl, $C_{1-4}$-alkoxy, characterized in that tetradepsipeptides of the formula (VII)

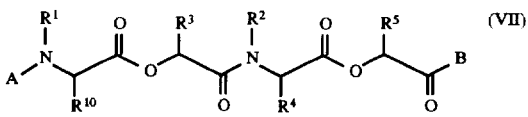

in which

A represents benzyl and

B represents tert.-butoxy, and $R^1$, $R^2$, $R^3$, $R^4$, $R^5$ and $R^{10}$ have the meaning given above, are hydrolysed in the presence of a diluent and a protic acid.

11. Process for the preparation of the tetradepsipeptides of the formula (VI)

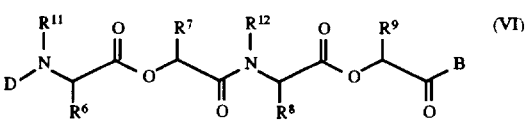

in which

D represents hydrogen and

B represents tert.-butoxy, and $R^{11}$, $R^2$ represent the same or different radicals selected from the group of $C_{1-8}$-alkyl, $C_{1-8}$-halogenoalkyl, $C_{3-6}$-cycloalkyl, aralkyl, aryl,

11

R[7], R[9] represent the same or different radicals selected from the group of hydrogen or straight-chain $C_{1-5}$-alkyl or branched $C_{4-7}$-alkyl which may optionally be hydroxy, $C_{1-4}$-alkoxy,

carboxyl (—COH), carboxamide, (—O—C—NH$_2$), imidazolyl, indolyl, guanidino, —SH or $C_{1-4}$-alkylthio and furthermore represent aryl or aralkyl or heteroarylmethyl which may be substituted by halogen, hydroxyl, $C_{1-4}$-alkyl, $C_{1-4}$-alkoxy, nitro or a —NR[13]R[14] group in which R[13] and R[14] independently from each other represent hydrogen or alkyl or together with the adjoining nitrogen atom forms a 5, 6 or 7-membered ring which is optionally interrupted by O, S or N and which is optionally $C_{1-4}$-alkyl substituted, R[6], R[8] represent the same or different radicals selected from the group of hydrogen, straight-chain or branched $C_{1-5}$-alkyl and represents $C_{2-6}$-alkenyl, $C_{3-7}$-cycloalkyl which may optionally be substituted by hydroxyl, $C_{1-4}$-alkoxy, carboxyl, carboxamide, imidazolyl, indolyl, guanidino, SH or $C_{1-4}$-alkylthio, and represent aryl, aralkyl or heteroarylmethyl which may be substituted by halogen, hydroxyl, $C_{1-4}$-alkyl, $C_{1-4}$-alkoxy, characterized in that tetradepsipeptides formula (VII)

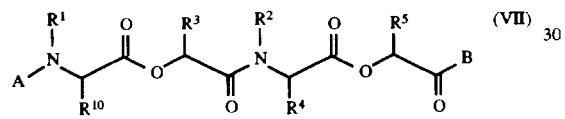

in which

A represents benzyl and

B represents tert.-butoxy, and

R[1], R[2], R[3], R[4], R[5] and R[10] possess the meaning given above, are subjected in the presence of a diluent and a catalyst to hydrogenolysis.

12. Tetradepsipeptides of the formula (VII)

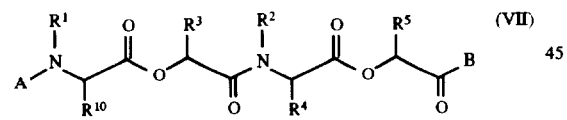

in which

A represents benzyl and

B represents tert.-butoxy, and

R[1], R[2] represent the same or different radicals selected from the group of $C_{1-8}$-alkyl, $C_{1-8}$-halogeno-alkyl, cycloalkyl, aralkyl, aryl, R[3], R[5] represent the same or different radicals selected from the group of hydrogen or straight-chain $C_{1-5}$-alkyl or branched $C_{4-7}$-alkyl which may optionally be substituted by hydroxyl, $C_{1-4}$-alkoxy,

carboxyl (—COH), carboxamide, (—O—C—NH$_2$), imidazolyl, indolyl, guanidino, —SH or $C_4$-alkylthio and furthermore represent aryl or aralkyl or heteroarylmethyl which may be substituted by halogen, hydroxyl, $C_{1-4}$-alkyl, $C_{1-4}$-alkoxy, nitro or

12 a —NR[13]R[14] group in which R[13] and R[14] independently from each other represent hydrogen or alkyl or together with the adjoining nitrogen atom forms a 5, 6 or 7-membered ring which is optionally interrupted by O, S or N and which is optionally $C_{1-4}$-alkyl substituted, R[4], R[10] represent the same or different radicals selected from the group of hydrogen, straight-chain or branched $C_{1-5}$-alkyl and represents $C_{2-6}$-alkenyl or $C_{3-7}$-cycloalkyl which may optionally be substituted by hydroxyl, $C_{1-4}$-alkoxy, carboxyl, carboxamide, imidazolyl, indolyl, guanidino, SH or $C_{1-4}$-alkylthio, and represent aryl,aralkyl or heteroarylmethyl which may be substituted by halogen, hydroxyl, $C_{1-4}$-alkyl, $C_{1-4}$-alkoxy.

13. Process for the preparation of the tetradepsipeptides of the formula (VII)

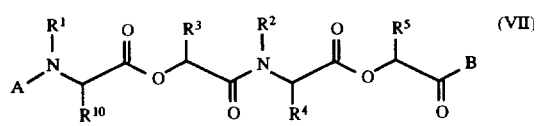

in which

A represents benzyl and

B represents tert.-butoxy, and

R[1], R[2] represent the same or different radicals selected from the group of $C_{1-8}$-alkyl, $C_{1-8}$-halogenoalkyl, $C_{3-6}$-cycloalkyl, aralkyl, aryl, R[3], R[5] represent the same or different radicals selected from the group of hydrogen or straight-chain $C_{1-5}$-alkyl or branched $C_{4-7}$-alkyl which may optionally be hydroxy, $C_{1-4}$-alkoxy,

carboxyl (—COH), carboxamide, (—O—C—NH$_2$), imidazolyl, indolyl, guanidino, —SH or $C_{1-4}$-alkylthio and furthermore represent aryl or aralkyl or heteroarylmethyl which may be substituted by halogen, hydroxyl, $C_{1-4}$-alkyl, $C_{1-4}$-alkoxy, nitro or a —NR[13]R[14] group in which R[13] and R[14] independetly from each other represent hydrogen or alkyl or together with the adjoining nitrogen atom forms a 5, 6 or 7-membered ring which is optionally interrupted by O, S or N and which is optionally $C_{1-4}$-alkyl substituted, R[4], R[10] represent the same or different radicals selected from the group of hydrogen, straight-chain or branched $C_{1-5}$-alkyl and represents $C_{2-6}$-alkenyl or $C_{3-7}$-cycloalkyl which may optionally be substituted by hydroxyl, $C_{1-4}$-alkoxy, carboxyl, carboxamide imidazolyl, indolyl, guanidino, SH or $C_{1-4}$-alkylthio and represent aryl, aralkyl or heteroarylmethyl which may be substituted by halogen, hydroxyl, $C_{1-4}$-alkyl $C_{1-4}$-alkoxy, characterized in that didepsipeptides of the formula (VIII

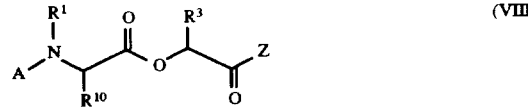

in which

A represents benzyl and

Z represents OH and $R^1$, $R^3$ and $R^{10}$ possess the meaniang given above and didepsipeptides of the formula (IX)

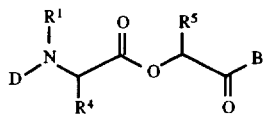

in which

D represents hydrogen and

B represents tert.-butoxy, and $R^2$, $R^4$ and $R^5$ possess the meaning given above, are condensed in a diluent in the presence of a coupling reagent.

Finally it has been found that the new octacyclodepsipeptides of the formula (I) and their acid addition salts and metal salt complexes possess very good anthelmintic properties and can be employed preferably in the veterinary sector. Surprisingly, the substances according to the invention exhibit, in the control of worm diseases, a better activity previously known compounds having a similar constitution and the same approach of action.

In the general formulae, alkyl denotes straight-chain or branched alkyl having preferably 1 to 9 carbon atoms, particularly preferably 1 to 5, and very particularly preferably 1 to 4, carbon atoms. The following may be mentioned by way of example: methyl, ethyl, n- and i-propyl, n-, i-, s- and t-butyl, pentyl, hexyl and octyl which are optionally substituted.

In the general formulae alkenyl denotes straight-chain or branched alkenyl having preferably 2 to 20, particularly 2 to 8 carbon atoms. The following may be mentioned by way of example: ethenyl, propenyl-(1), propenyl-(2), butenyl-(3) which are optionally substituted.

In the general formulae cycloalkyl denotes mono-, bi- or tri-cyclic cycloalkyl having preferably 3 to 10, particularly 3, 5 or 6 ring carbon atoms. The following may be mentioned by way of example: cyclopropyl, cyclobutyl, cyclopentyl, cyclohexyl, cycloheptyl which are optionally substituted.

Alkoxy in the general formulae is straight-chain or branched alkoxy having preferably 1 to 6, in particular 1 to 4, carbon atoms. Methoxy, ethoxy, propoxy, butoxy and their isomers, such as, for example, i-propoxy, and i-, s- and t-butoxy, may be mentioned by way of example, and may be substituted.

Alkylthio in the general formulae is straight-chain or branched alkylthio having preferably 1 to 6, particularly preferably 1 to 4, carbon atoms, for example optionally substituted methylthio, ethylthio, propylthio, butylthio, pentylthio and their isomers, such as, for example, i-propylthio, i-, s- and t-butylthio. Halogenoalkyl in the general formulae has 1 to 4, particularly 1 or 2 carbon-atoms and 1 to 9, particularly 1to 5 same or different halogen atoms. As halogen atoms are mentioned fluorine, chlorine The following may be mentioned by way of example tri-fluoromethyl, chloro-difluoromethyl, 2,2,2-trifluoroethyl, pentafluoroethyl, perfluoro-t-butyl.

Aryl in the general formulae is aryl having preferably 6 or 10 carbon atoms in the aryl moiety. Unsubstituted or substituted phenyl or naphthyl, in particular phenyl, may be mentioned as being preferred and may be substituted.

Arylalkyl in the general formulae is optionally substituted in the alkyl- or in the aryl part, it has preferably 6 or 10, particularly 6 carbon atoms in the aryl part, mention being made of naphthyl and phenyl, very particularly mentioned is phenyl, in the alkyl part 1 to 4 carbon atoms, particularly 1 or 2 carbon atoms may be mentioned. Benzyl or phenethyl may be mentioned by way of example. Heteroaryl in the general formulae is preferably a 5 to 7-membered heteroaromatic, optionally benzo-fused ring which contains one or more hetero atoms, preferably 1 to 3 identical or different hetero atoms. Preferred hetero atoms which may be metnioned are oxygen, sulphur and nitrogen. The following may be mentioned as particularly preferred for heteroaryl: pyridyl, pyrimidinyl, pyridazinyl, pyrazinyl, furyl, thienyl, pyrazolyl, imidazolyl, triazolyl, isoxazolyl, isothiazolyl, pyrrolyl, piperazinyl, triazinyl, oxazinyl, oxepinyl, thiepinyl, diazepinyl, thiazolyl, thiadiazolyl, oxadiazolyl, oxazolyl, quinolyl, isoquinolyl, benzoxazolyl, benzothiazolyl and benzimidazolyl. The heteroaryl ring can itself be substituted.

In the general formulae optionally substituted radicals may carry one or more, preferably 1 to 3, particularly 1 to 2 same or different substituents. The following substituents may be mentioned as examples:

Alkyl with preferably 1 to 4 particularly 1 to 2 carbon atoms, methyl, ethyl, n- and i-propoyl, n-, i- and t-butyl are named as examples; alkoxy with preferably 1 to 4 particulary 1 to 2 carbon atoms, methoxy, ethoxy, n- or i-propoxy, n-, i- or t-butoxy are named as examples; alkylthio with preferably 1 to 4 particularly 1 to 2 carbon atoms, methylthio, ethylthio, n- or i-propylthio, n-, i- or t-butylthio are named as examples; alkylsulfinyl or alkylsulfonyl with preferably 1 to 4 particularly 1 to 2 carbon atoms like methylsulfinyl, methylsul-fonyl, ethylsulfinyl, ethylsulfonyl; arylsulfonyl with 6 to 10 carbon atoms in the aryl part like phenylsulfonyl; halogenoalkyl, halogenoalkoxy, halogenoalkylthio, halogenoalkyl-sulphinyl and/or halogenoalkylsulphonyl (having in each case preferably 1 to 4, in particular 1 or, 2, carbon atoms and in each case 1 to 6, in particular 1 to 3, identical or different halogen atoms, in particular fluorine and/or chlorine atoms), trifluormethyl, difluormethyl, trifluormethylsulfinyl, trifluormethylsulfonyl, perfluor n, s, t-butylsulfonyl may be mentioned by way of example. Further substituents which may be mentioned are hydroxy, halogen preferably fluorine, chlorine, cyano, nitro, amino, formimino,

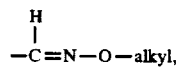

mono- or dialkylamino having 1 or 2 alkyl groups, each of which can be straight-chain or branched and contain preferably 1 to 5, in particular 1 to 4 and particularly preferably 1 to 3, carbon atoms, mention being made of methyl, ethyl and n- and i-propyl; dimethylamino, diethylamino, di-n-propylamino and di-i-propylamino may be mentioned by way of example; further substituents which may be mentioned are acyl, aryl, aryloxy, heteroaryl, heteroarylalkyl, heteroaryloxy which may be substituted themselves by one of the above mentioned substituents.

It is preferred to employ compounds of the formula (I) in which $R^1$, $R^2$, $R^{11}$ and $R^{12}$, independently of one another, represent methyl, ethyl, propyl, butyl or phenyl which is optionally substituted by halogen, $C_{1-4}$-alkyl, OH, $C_{1-4}$-alkoxy, and represent benzyl or phenylethyl, each of which may optionally be substituted by the radicals given for phenyl;

$R^3$ to $R^{10}$ have the meaning given above.

Particularly preferred compounds of the formula (I) are those in which $R^1$, $R^2$, $R^{11}$ and $R^{12}$, independently of one another, represent methyl, ethyl, propyl, isopropyl or n-, s-, t-butyl, $R^3$, $R^5$, $R^7$, $R^9$ represents hydrogen, straight-chain $C_{1-5}$-alkyl or branched $C_{4-5}$-alkyl, in particular methyl, ethyl, propyl, which may optionally be substituted by $C_{1-4}$-alkoxy, in particular methoxy, ethoxy, imidazolyl, indolyl or $C_{1-4}$-alkylthio, in particular methylthio, ethylthio, and represents isobutyl or s-butyl and furthermore represents phenyl, benzyl or phenethyl or heteroarylmethyl each of which may optionally be substituted by halogen in particular chlorine, nitro or a $-NR^{13}R^{14}$ group in which $R^{13}$ and $R^{14}$ independently from each other represent hydrogen or alkyl or together with the adjoining nitrogen atom forms a 5, 6 or 7-membered ring which is optionally interrupted by O, S or N and which is optionally $C_{1-4}$-alkyl substituted, $R^4$, $R^6$, $R^8$, $R^{10}$, independently of one another, represent hydrogen, methyl, ethyl, n-propyl, n-butyl, vinyl, cyclohexyl, each of which may optionally be substituted by methoxy, ethoxy, imidazolyl, indolyl, methylthio, ethylthio, and represent isopropyl, s-butyl furthermore represent optionally halogen-substituted phenyl, benzyl, phenyl ethyl or heteroarylmethyl.

In Process 2, octadepsipeptides are cyclized in the presence of diluents and suitable coupling reagents.

Suitable coupling reagents are all compounds which are suitable for linking an amide bond (cf. e.g.: Houben-Weyl, Methoden der organischen Chemie, volume 15/2; Bodanzky et al., Peptide Synthesis 2nd ed., Wiley and Sons, New York 1976).

The following reagents and methods are preferably considered, the active ester method with pentaf luorophenol (PfP), N-hydroxy-succinimide, 1-hydroxybenzotriazole, coupling with carbodiimides such as dicyclohexylcarbodimide or N'-(3 -dimethylaminopropyl)-N-ethyl-carbodiimide (Ebc) and the mixed anhydride method or coupling with phosphonium reagents such as benzotriazol-1-yl-oxy-tris (dimethylaminophosphonium) hexafluorophosphate (BOP), bis (2-oxo-3-oxazolidinyl)-phosphonium acid chloride (BOP-Cl) or with phosphonate reagents such as diethyl cyanophosphonate (DEPc) and diphenylphosphoryl azide (DPPA).

Particular preference is given to the coupling with bis (2-oxo-3-oxazolidinyl) -phosphonium acid chloride (BOP-Cl) and N'-(3-dimethylaminopropyl)-N-ethylcarbodiimide (EDC) in the presence of 1-hydroxybenzotriazole (HOBt).

The reaction is carried out at temperatures from 0°–150° C., preferably at 20°–100° C., particularly preferably at room temperature.

Suitable diluents are all inert organic solvents. These include, in particular, aliphatic and aromatic, optionally halogenated hydrocarbons such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, also ethers such as diethyl- and dibutyl ether, glycol dimethyl ether and diglycol dimethyl ether, tetrahydrofuran and dioxane, furthermore ketones such as acetone, methyl ethyl, methyl isopropyl and methyl isobutyl ketone, in addition esters such as methyl acetate and ethyl acetate, also nitriles, for example acetonitrile and propionitrile, benzonitrile, glutaronitrile, moreover amides, for example dimethylformamide, dimethylacetamide and N-methylpyrrolidone, and dimethyl sulphoxide, tetramethylene sulphone and hexamethylphosphoric triamide.

The compounds of the formulae (II) and the coupling reagents are employed in a ratio of from 1:1 to 1:1.5 with respect to one another. An approximately equimolar ratio is preferred.

After reaction has taken place, the diluent is distilled off and the compounds of the formula (I) are purified in a conventional manner, for example by chromatography.

The reaction according to Process 4 is carried out using hydrogenating agents.

The preferred hydrogenating agent which may be mentioned is hydrogen in the presence of the conventional hydrogenation catalysts, for example Raney nickel, palladium and platinum.

The process is preferably carried out using diluents. Suitable diluents in this context are practically all inert organic solvents. These include, preferably, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl and dibutyl ether, methyl tert.-butyl ether, glycol dimethyl ether and diglycol dimethyl ether, tetrahydrofuran and dioxane, esters such as methyl acetate and ethyl acetate, nitriles, for example acetonitrile and propionitrile, amides, for example dimethylformamide, dimethylacetamide and N-methyl-pyrrolidone and dimethyl sulphoxide, tetramethylene sulphone and hexamethylphosphoric triamide; and also alcohols such as methanol, ethanol, propanol, isopropanol, butanol, isobutanol, sec.-butanol, tert.-butanol, pentanol, isopentanol, sec.-pentanol and tert.-pentanol, and water.

The reaction temperatures in the process according to the invention can be varied over a relatively wide range. The temperatures employed are in general between –20° C. and +200° C., preferably between 0° C. and 120° C.

The process according to the invention is generally carried out under atmospheric pressure. However, it is also possible to work under increased pressure, in general between 10 and 100 bar.

The reaction according to Process 6 is preferably carried out using diluents.

Suitable diluents are virtually all inert organic solvents. These include, preferably, aliphatic and aromatic, optionally halogenated hydrocarbons, benzine, ligroin, benzene, toluene, xylene, methylene chloride, ethylene chloride, chloroform, carbon tetrachloride, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl, methyl isopropyl and methyl isobutyl ketone, esters such as methyl acetate and ethyl acetate, nitriles, for example acetonitrile and propionitrile, amides, for example dimethylformamide, dimethylacetamide and N-methyl-pyrrolidone, and dimethyl sulphoxide, tetramethylene sulphone and hexamethylphosphoric triamide.

The reaction is carried out in the presence of inorganic or organic protic acids.

Examples of these which may be mentioned are: hydrochloric acid, sulphuric acid, trifluoroacetic acid, acetic acid, formic acid.

The reaction is carried out at temperatures of between –20° and +50° C., preferably at between –10° and +20° C., under atmospheric pressure or increased pressure. Atmospheric pressure is preferably used.

The reaction according to Process 8 is preferably carried out using diluents.

Suitable diluents are virtually all inert organic solvents. These include, preferably, aliphatic and aromatic, optionally halogenated hydrocarbons, benzine, ligroin, benzene, toluene, xylene, methylene chloride, ethylene chloride, chloroform, carbon tetrachloride, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl, methyl isopropyl and methyl isobutyl ketone, esters such as methyl acetate and ethyl acetate, nitriles, for example acetonitrile and propionitrile, amides, for example dimethylformamide, dimethylacetamide and N-methylpyrrolidone, and dimethyl sulphoxide, tetramethylene sulphone and hexamethylphosphoric triamide.

The reaction is carried out in the presence of inorganic or organic acid acceptors.

Examples of these which may be mentioned are:

Alkali metal hydroxides, for example sodium hydroxide and potassium hydroxide, alkaline earth metal hydroxides, for example calcium hydroxide, alkali metal carbonates and alcoholates such as sodium carbonate and potassium carbonate, sodium methylate or ethylate and potassium methylate or ethylate, also aliphatic, aromatic or heterocyclic amines, for example triethylamine, pyridine, 1,5-diazabicyclo-[4.3.0]-non-5-ene (DBN), 1,8-diazabicyclo-[5.4.0]-undec-7-ene (DBU) and 1,4-diazabicyclo-[2.2.2]-octane (DABCO), ethyl-diisopropylamine.

The reaction is carried out at temperatures of between 10° and 150° C., preferably at between 20° to 100° C. at atmospheric pressure or increased pressure. Atmospheric pressure is preferably used.

Process 11 is carried out as indicated above for the procedure of Process 6.

The process according to the invention described under 12 is carried out as indicated for Process 4.

Process 14 is carried out as indicated above for the procedure of Process 8.

While being of favourable toxicity for warm-blooded creatures, the active substances are suitable for controlling pathogenic endoparasites which occur in humans and, in the keeping and rearing of animals, in livestock, breeding stock, zoo animals, laboratory animals, animals for experimentation and hobby animals. In this context they are active against all or individual development stages of the pests, and against resistant and normally sensitive species. The control of the pathogenic endoparasites is intended to reduce disease, deaths and reductions in yield (e.g. in the production of meat, milk, wool, hides, eggs, honey etc.), so that the use of the active substance enables the keeping of animals to be more economic and more simple. The pathogenic endoparasites include cestodes, trematodes, nematodes, Acantocephala in particular:

From the order of the Pseudophyllidea e.g.: *Diphyllobothrium spp., Spirometra spp., Schistocephalus spp., Ligula spp., Bothridium spp., Diphlogonoporus spp.*

From the order of the Cyclophyllidea e.g.: *Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.*

From the subclass of the Monogenea e.g.: *Gyrodactylus spp., Dactylogyrus spp., Polystoma spp.*

From the subclass of the Digenea e.g.: *Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinopary-*

*phium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp-, Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp. Metorchis spp., Heterophyes spp., Metagonimus spp.*

From the order of the Enoplida e.g.: *Trichuris spp., Capillaria spp., Trichomosoides spp., Trichinella spp.*

From the order of the Rhabditia e.g.: *Micronema spp., Strongyloides spp.*

From the order of the Strongylida e.g.: *Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., protostronglyus spp., Neostrongylus spp., Cystocaulus spp., Pneumostrongylus spp., Spicocaulus spp., Elaphostrongylus spp. Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.*

From the order of the Oxyurida e.g.: *Oxyuris spp., Enterobius spp., Passalurus spp., Syphacia spp., Aspiculuris spp., Heterakis spp.*

From the order of the Ascaridia e.g.: *Ascaris spp., Toxascaris spp., Toxocara spp., Parascaris spp., Anisakis spp., Ascaridia spp.*

From the order of the Spirurida e.g.: *Gnathostoma spp., Physaloptera spp., Thelazia spp., Gongylonema spp., Habronema spp., Parabronema spp., Draschia spp., Dracunculus spp.*

From the order of the Filariida e.g.: *Stephanofilaria spp., Parafilaria spp., Setaria spp., Loa spp., Dirofilaria spp., Litomosoides spp., Brugia spp., Wuchereria spp., Onchocerca spp.*

From the order of the Gigantorhynchida e.g.: *Filicollis spp., Moniliformis spp., Macracanthorhynchus spp., Prosthenorchis spp.*

The livestock and breeding stock animals include mammals, for example cattle, horses, sheep, pigs, goats, camels, water buffalo, donkeys, rabbits, fallow deer, reindeer, fur animals, for example mink, chinchilla, racoon, birds, for example chickens, geese, turkeys, ducks, freshwater and salt-water fish, for example trout, carp, eels, reptiles, insects, for example honey bees, and silkworms.

Laboratory animals and those for experimentation include mice, rats, guinea-pigs, golden hamsters, dogs and cats.

Hobby animals include dogs and cats.

Administration can be carried out both prophylactically and therapeuticaly.

The administration of the active substances is carried out, directly or in the form of suitable formulations, enterally, parenterally, dermally, nasally, by treating the surrounding area or with the aid of shaped articles containing active substance, for example strips, plates, tapes, collars, ear-tags, limb bands, marking devices.

The enteral administration of the active substances is effected, for example, orally in the form of powder, tablets, capsules, pastes, potions, granules, solutions suitable for oral administration, suspensions and emulsions, boli, medicated feed or drinking water. The dermal application is effected, for example, by dipping, spraying or pouring-on and spotting-on. The parenteral administration is effected, for example, by injection (intramuscular, subcutaneous, intravenous, intraperitoneal) or by means of implants.

Suitable formulations are:

Solutions such as solutions for injection, oral solutions, concentrates for oral administration after dilution, solutions for use on the skin or in body cavities, pour-on formulations, gels;

Emulsions and suspension for oral or dermal administration and for injection; semi-solid formulations;

Formulations in which the active substance is processed in an ointment base or in an oil-in-water or water-in-oil emulsion base;

Solid formulations such as powders, premixes or concentrates, granules, pellets, tablets, boli, capsules; aerosols and inhalation products, shaped articles containing active substance.

Injection solutions are administered intravenously, intramuscularly and subcutaneously.

Injection solutions are prepared by dissolving the active substance in a suitable solvent and adding, if appropriate, additives such as solubilizers, acids, bases, buffer salts, antioxidants, preservatives. The solutions are subjected to sterile filtration and placed in containers.

Solvents which may be mentioned are: physiologically compatible solvents such as water, alcohols such as ethanol, butanol, benzyl acohol, glycerol, propylene glycol, polyethylene glycols, N-methyl-pyrrolidone, and mixtures thereof.

If appropriate, the active substances can also be dissolved in physiologically compatible vegetable or synthetic oils suitable for injection.

Solubilizers which may be mentioned are: solvents which promote the dissolution of the active substance in the principle solvent or prevent its precipitation. Examples are polyvinyl pyrrolidone, polyoxyethylated castor oil, polyoxyetbylated sorbitol esters.

Preservatives are: benzyl alcohol, trichlorobutanol, p-hydroxybenzoates, n-butanol.

Oral solutions are administered directly. Concentrates are administered orally after prior dilution to the use concentration. Oral solutions and concentrates are prepared as described above for the injection solutions, although sterile conditions can be dispensed with.

Solutions for use on the skin are applied in drops, painted on, rubbed in or sprayed on. These solutions are prepared as described above for the injection solutions.

It may be advantageous to add thickeners during the preparation. Thickeners are: inorganic thickeners such as bentonites, colloidal silica, aluminium monostearate, organic thickeners such as cellulose derivatives, polyvinyl alcohols and copolymers thereof, acrylates and metacrylates.

Gels are applied to or painted onto the skin or introduced into body cavities. Gels are prepared by the addition, to solutions which have been prepared as described for the injection solutions, of a quantity of thickener which ensures that a clear mass of cream-like consistency is formed. The thickeners employed are the thickeners indicated above.

Pour-on formulations are poured or sprayed onto limited areas of the skin, the active substance penetrating the skin and acting systemically.

Pour-on, formulations are prepared by dissolving, suspending or emulsifying the active substance in suitable skin-compatible solvents or solvent mixtures. If desired, further auxiliaries such as colorants, absorption-promoting substances, antioxidants, light stabilizers, adhesives are added.

Solvents which can be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methyl-pyrrolidone, 2,2-dimethyl-4-oxy-methylene-1,3-dioxolane.

Colorants are all colorants permitted for use with animals, and may be dissolved or suspended.

Absorption-promoting substances are, for example, DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Light stabilizers are, for example, Novantisol acid.

Adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active substance either in the hydrophobic or in the hydrophillic phase and homogenizing this phase, with the aid of suitable emulsifiers and, if appropriate; other auxiliaries such as colorants, absorption-promoting substances, preservatives, antioxidants, light stabilizers, viscosity-increasing substances, with the solvent of the other phase.

As the hydrophobic phase (oils) there may be mentioned: paraffin oils, silicone oils, natural vegetable oils such as sesame oil, almond oil, castor oil, synthetic triglycerides such as caprylic/capric acid bigylceride, a triglyceride mixture with plant fatty acids of chain length $C_{8-12}$ or other specially selected natural fatty acids, partial glyceride mixtures of saturated or unsaturated fatty acids, if appropriate together with fatty acids containing hydroxyl groups, mono- and diglycerides of $C_8/C_{10}$ fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}-C_{18}$, isopropyl myristate, isopropyl palmitate, caprylic/capric acid esters of saturated fatty alcohols of chain length $C_{12}-C_{18}$, isopropyl stearate, oleyl oleate, decyl oleate, ethyl oleate, ethyl lactate, wax-like fatty acid esters such as synthetic duck oil-gland fat, dibutyl phthalate, diisopropyl adipate, ester mixtures related to the latter, etc.

Fatty alcohols such as isotridecyl alcohol, 2-octyldodecanol, cetylstearyl alcohol, oleyl alcohol.

Fatty acids, for example oleic acid, and mixtures thereof.

As the hydrophillic phase there may be mentioned: water, alcohols, for example propylene glycol, glycerol, sorbitol, and mixtures thereof.

Emulsifiers which may be mentioned are: nonionic surfactants, e.g. polyoxyethylated castor oil, polyoxyethylated sorbitol monooleate, sorbitol monostearate, glycerol monostearate, polyoxyethyl stearate, alkylphenol polyglycol ether;

ampholytic surfactants such as di-Na-N-lauryl-β-iminodipropionate or lecithin;

anionic surfactants such as Na-lauryl sulphate, fatty alcohol ether sulphates, mono/dialkylpolyglycol ether orthophosphoric acid ester monoethanol amine salt;

cationic surfactants such as cetyltrimethylammonium chloride.

Further auxiliaries which may be mentioned are: viscosity-increasing and emulsion-stabilizing substances such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica, or mixtures of the substances listed.

Suspensions can be administered orally, dermally or by injection. They are prepared by suspending the active substance in a carrier liquid, with the optional addition of further auxiliaries such as wetting agents, colorants, absorption-promoting substances, preservatives, antioxidants light stabilizers.

Carrier liquids which may be mentioned are all homogeneous solvents and solvent mixtures.

Wetting agents (dispersants) which may be mentioned are the surfactants given above.

Further auxiliaries which may be mentioned are those given above.

Semi-solid formulations may be administered orally or dermally. They differ from the above-described suspensions and emulsions only in their higher viscosity.

For the preparation of solid formulations, the active substance is mixed with suitable carrier substances with the optional addition of auxiliaries, and brought into the desired form.

Carrier substances which may be mentioned are all physiologically compatible solid inert substances. Suitable substances are inorganic and organic substances. Examples of inorganic substances are common salt, carbonates such as calcium carbonate, hydrogen carbonates, aluminium oxides, silicic acids, argillaceous earths, precipitated or colloidal silicon dioxide, phosphates.

Examples of organic substances are sugar, cellulose, nutrients and feedstuffs such as milk powder, animal meals, corn meals and wholemeals, starches.

Auxiliaries are preservatives, antioxidants, colorants, which have already been listed above.

Other suitable auxiliaries are lubricants and glidants, for example magnesium stearate, stearic acid, talc, bentonites, disintegration-promoting substances such as starch or crosslinked polyvinylpyrrolidone, binders, for example starch, gelatin or linear polyvinylpyrrolidone, and dry binders such as microcrystalline cellulose.

The active substances can also be present in the formulations as a mixture with synergists or with other active substances which act against pathogenic endoparasites. Examples of such active substances are L-2,3,5,6-tetrahydro-6-phenyl-imidazothiazole, benzimidazole carbamates, praziquantel, pyrantel, febantel.

Ready-to-use formulations contain the active substance in concentrations of from 10 ppm–20 per cent by weight, preferably from 0.1–10 per cent by weight.

Formulations which are diluted prior to use contain the active substance in concentrations of from 0.5–90% by weight, preferably from 5 to 50 per cent by weight.

In general it has proven advantageous to administer amounts of from approximately 1 to approximately 100 mg of active substance per kg of body weight per day in order to achieve effective results.

EXAMPLE A

In Vivo Nematode Test
Haemonchus Contortus/Sheep

Sheep experimentally infected with *Haemonchus contortus* were treated after the end of the pre-patency period of the parasites. The active compounds were administered orally (p.o) as pure active compound in gelatin capsules or intravenously (i.v.) as a solution.

The degree of effectiveness is determined by quantitatively counting the worm eggs excreted with the faeces, before and after treatment.

Complete cessation of the excretion of eggs after the treatment means that the worms have been expelled or are so severely damaged that they can no longer produce any eggs (effective dose).

The active substances tested and the active doses (effective dose) are evident from the following table:

| | Effective dose in mg/kg | |
|---|---|---|
| Example No. | p.o. | i.v. |
| 5 | 5 | |
| 4 | | 1 |

The preparation of the active substances according to the invention is evident from the following examples.

PREPARATION EXAMPLES

1. Preparation of the Compounds of the Formula (I) According to Process 2

BOP-Cl (0.124 mmol) was added at 0° C. to a solution of the compound of the formula II (0.104 mmol) and Hünig base (0.258 mmol) in dichloromethane (100 ml) and the mixture was subsequently stirred for 24 h at room temperature. After this time, the same quantities of BOP-Cl and base were added, and the mixture was stirred for a further 24 h. The solution was washed twice with sat. sodium hydrogen carbonate solution, dried over sodium sulphate and concentrated. The residue was purified by column chromatography using the eluent cyclohexane-ethyl acetate 2:1.

Compounds of the formula (I) were obtained in which the substituents have the following meaning:

TABLE 1

| Nr. | R$^1$ | R$^{12}$ | R$^9$ | R$^8$ | R$^7$ | R$^6$ | R$^5$ | R$^4$ | R$^3$ | R$^{10}$ | R$^{11}$ | R$^2$ | FAB-MS m/z (%) |
|---|---|---|---|---|---|---|---|---|---|---|---|---|---|
| 1 | Et | Et | Me | s-Bu | Bn | s-Bu | Me | s-Bu | Bn | s-Bu | Et | Et | |
| 2 | Propyl | Propyl | Me | s-Bu | Bn | s-Bu | Me | s-Bu | Bn | s-Bu | Propyl | Propyl | |
| 3 | i-Propyl | i-Propyl | Me | s-Bu | Bn | s-Bu | Me | s-Bu | Bn | s-Bu | i-Propyl | i-Propyl | |
| 4 | Me | Me | Me | s-Bu | Bn | s-Bu | Me | s-Bu | Bn | s-Bu | Me | Me | 948 (82, (M + H)$^+$) |
| 5 | Me | Me | Me | i-Pr | Bn | i-Pr | Me | i-Pr | Bn | i-Pr | Me | Me | 915 (100, (M + Na)$^+$), 893 (55, (M + H)$^+$), |
| 6 | Me | Me | Me | Bn | Bn | Bn | Me | Bn | Bn | Bn | Me | Me | 1107 (100, (M + Na)$^+$), 1085 (8, (M + H)$^+$) |
| 7 | Me | Me | Me | s-Bu | 2-Cl—Bn | s-Bu | Me | s-Bu | 2-Cl—Bn | s-Bu | Me | Me | |
| 8 | Me | Me | Me | s-Bu | 2-Cl—Bn | s-Bu | Me | s-Bu | 3-Cl—Bn | s-Bu | Me | Me | |
| 9 | Me | Me | Me | s-Bu | 4-Cl—Bn | s-Bu | Me | s-Bu | 4-Cl—Bn | s-Bu | Me | Me | |
| 10 | Propyl | i-Propyl | Me | s-Bu | -Bn | s-Bu | Me | s-Bu | -Bn | s-Bu | Propyl | i-Propyl | |
| 11 | Me | Me | Me | i-Bu | 4-Cl—Bn | i-Bu | Me | i-Bu | 4-Cl—Bn | i-Bu | Me | Me | 1018 (30, M$^+$) |
| 12 | Me | Me | Me | i-Bu | 3-Cl—Bn | i-Bu | Me | i-Bu | 3-Cl—Bn | i-Bu | Me | Me | |
| 13 | Me | Me | Me | i-Bu | 2-Cl—Bn | i-Bu | Me | i-Bu | 2-Cl—Bn | i-Bu | Me | Me | 1018 (90, M$^+$) |
| 14 | Me | Me | Me | i-Bu | 4-Cl—Bn | i-Bu | Me | i-Bu | Bn | i-Bu | Me | Me | |
| 15 | Me | Me | Me | i-Bu | 3-Cl—Bn | i-Bu | Me | i-Bu | Bn | i-Bu | Me | Me | |
| 16 | Me | Me | Me | i-Bu | 2-Cl—Bn | i-Bu | Me | i-Bu | Bn | i-Bu | Me | Me | 383 (28, (M + H)$^+$) |
| 17 | Me | Me | Me | i-Bu | 4-NO$_2$—Bn | i-Bu | Me | i-Bu | 4-NO$_2$—Bn | i-Bu | Me | Me | 1039 (100, (M + H)$^+$) |
| 18 | Me | Me | Me | i-Bu | 4-NO$_2$—Bn | i-Bu | Me | i-Bu | Bn | i-Bu | Me | Me | |
| 19 | Me | Me | Me | Me | Bn | Me | Me | Me | Bn | Me | Me | Me | 781 (100, M$^+$) |
| 20 | Me | Me | Me | Me | Bn | Me | Me | i-Bu | Bn | i-Bu | Me | Me | 865 (38, (M + H)$^+$) |
| 21 | Me | Me | Me | Pr | Bn | Pr | Me | Pr | Bn | Pr | Me | Me | 893 (100, (M + H)$^+$) |
| 22 | Me | Me | Me | Pr | Bn | Pr | Me | i-Bu | Bn | i-Bu | Me | Me | 921 (100, M$^+$) |
| 23 | Me | Me | Me | i-Bu | Bn | i-Bu | H | i-Bu | H | i-Bu | Me | M& | 845 (100, M$^+$) |

Me = Methyl
Et = Ethyl
s-Bu = sek.-Butyl
Bn = Benzyl
Pr = Propyl
i-Bu = iso-Butyl
i-Pr = iso-Propyl

2. Preparation of the Compounds of the Formula (II) According to Process 4

A solution of a compound of the formula III (1.222 mmol) in ethanol (50 ml) was hydrogenated in the presence of Pd(OH)$_2$/C (20%; 200 mg) until hydrogen uptake had finished (about 2 h). After the catalyst had been filtered off, pure compound of the formula II was obtained which was reacted further without additional purification.

In accordance with this procedure, compounds of the formula (II) were obtained in which the substituents have the meaning given in Table 1.

TABLE 2

| Nr. | R$^1$ | R$^{12}$ | R$^9$ | R$^8$ | R$^7$ | R$^6$ | R$^5$ | R$^4$ | R$^3$ | R$^{10}$ | R$^{11}$ | R$^2$ |
|---|---|---|---|---|---|---|---|---|---|---|---|---|
| 24 | Et | Et | Me | s-Bu | Bn | s-Bu | Me | s-Bu | Bn | s-Bu | Et | Et |
| 25 | Propyl | Propyl | Me | s-Bu | Bn | s-Bu | Me | s-Bu | Bn | s-Bu | Propyl | Prop |
| 26 | i-Propyl | i-Propyl | Me | s-Bu | Bn | s-Bu | Me | s-Bu | Bn | s-Bu | i-Propyl | i-Pr |
| 27 | Me | Me | Me | s-Bu | Bn | s-Bu | Me | s-Bu | Bn | s-Bu | Me | Me |
| 28 | Me | Me | Me | i-Propyl | Bn | i-Propyl | Me | i-Propyl | Bn | i-Propyl | Me | Me |
| 29 | Me | Me | Me | Bn | Bn | Bn | Me | Bn | Bn | Bu | Me | Me |
| 30 | Me | Me | Me | s-Bu | 2-Cl—Bn | s-Bu | Me | s-Bu | 2-Cl—Bn | s-Bu | Me | Me |
| 31 | Me | Me | Me | s-Bu | 3-Cl—Bn | s-Bu | Me | s-Bu | 3-Cl—Bn | s-Bu | Me | Me |
| 32 | Me | Me | Me | s-Bu | 4-Cl—Bn | s-Bu | Me | s-Bu | 4-Cl—Bn | s-Bu | Me | Me |
| 33 | Propyl | i-Propyl | Me | s-Bu | Bn | s-Bu | Me | s-Bu | Bn | s-Bu | Propyl | i-Pr |
| 34 | Me | Me | Me | i-Bu | 4-Cl—Bn | i-Bu | Me | i-Bu | 4-Cl—Bn | i-Bu | Me | Me |
| 35 | Me | Me | Me | i-Bu | 3-Cl—Bn | i-Bu | Me | i-Bu | 3-Cl—Bn | i-Bu | Me | Me |
| 36 | Me | Me | Me | i-Bu | 2-Cl—Bn | i-Bu | Me | i-Bu | 2-Cl—Bn | i-Bu | Me | Me |
| 37 | Me | Me | Me | i-Bu | 4-Cl—Bn | i-Bu | Me | i-Bu | Bn | i-Bu | Me | Me |
| 38 | Me | Me | Me | i-Bu | 3-Cl—Bn | i-Bu | Me | i-Bu | Bn | i-Bu | Me | Me |
| 39 | Me | Me | Me | i-Bu | 2-Cl—Bn | i-Bu | Me | i-Bu | Bn | i-Bu | Me | Me |
| 40 | Me | Me | Me | i-Bu | 4-NO$_2$—Bn | i-Bu | Me | i-Bu | 4-NO$_2$—Bu | i-Bu | Me | Me |
| 41 | Me | Me | Me | i-Bu | 4-NO$_2$—Bn | i-Bu | Me | i-Bu | Bn | i-Bu | Me | Me |
| 42 | Me | Me | Me | Me | Bn | Me | Me | Me | Bn | Me | Me | Me |
| 43 | Me | Me | Me | Me | Bn | Me | Me | i-Bu | Bn | i-Bu | Me | Me |
| 44 | Me | Me | Me | Pr | Bn | Pr | Me | Pr | Bn | Pr | Me | Me |

TABLE 2-continued

| Nr. | $R^1$ | $R^{12}$ | $R^9$ | $R^8$ | $R^7$ | $R^6$ | $R^5$ | $R^4$ | $R^3$ | $R^{10}$ | $R^{11}$ | $R^2$ |
|---|---|---|---|---|---|---|---|---|---|---|---|---|
| 45 | Me | Me | Me | Pr | Bn | Pr | Me | i-Bu | Bn | i-Bu | Me | Me |
| 46 | Me | Me | Me | i-Bu | Bn | i-Bu | H | i-Bu | H | i-Bu | Me | Me |

Me = Methyl
Et = Ethyl
s-Bu = sek.-Butyl
Bn = Benzyl
Pr = Propyl
i-Bu = iso-Butyl
i-Pr = iso-Propyl

4. Preparation of the Compounds of the Formula (III) According to Process 6

HCl gas was passed into a solution of the tert. butyl ester of the formula (IV) (1.609 mmol) in dichloromethane (40 ml) for 1.5 h at 0° C. The mixture was then heated to room temperature and subsequently stirred for 12 h. The solution was concentrated on a rotary evaporator and dried under a high vacuum. The residue was reacted without further purification.

Analogously to this procedure, compounds of the formula (III) were obtained in which the substituents have the following meaning:

TABLE 3

| Nr. | $R^1$ | $R^{12}$ | $R^9$ | $R^8$ | $R^7$ | $R^6$ | $R^5$ | $R^4$ | $R^3$ | $R^{10}$ | $R^{11}$ | $R^2$ | A |
|---|---|---|---|---|---|---|---|---|---|---|---|---|---|
| 47 | Et | Et | Me | s-Bu | Bn | s-Bu | Me | s-Bu | Bn | s-Bu | Et | Et | Bn |
| 48 | Propyl | Propyl | Me | s-Bu | Bn | s-Bu | Me | s-Bu | Bn | s-Bu | Propyl | Propyl | Bn |
| 49 | i-Propyl | i-Propyl | Me | s-Bu | Bn | s-Bu | Me | s-Bu | Bn | s-Bu | i-Propyl | i-Propyl | Bn |
| 50 | Me | Me | Me | s-Bu | Bn | s-Bu | Me | s-Bu | Bn | s-Bu | Me | Me | Bn |
| 51 | Me | Me | Me | i-Propyl | Bn | i-Propyl | Me | i-Propyl | Bn | i-Propyl | Me | Me | Bn |
| 52 | Me | Me | Me | Bn | Bn | Bn | Me | Bn | Bn | Bn | Me | Me | Bn |
| 53 | Me | Me | Me | s-Bu | 2-Cl—Bn | s-Bu | Me | s-Bu | 2-Cl—Bn | s-Bu | M | Me | Bn |
| 54 | Me | Me | Me | s-Bu | 3-Cl—Bn | s-Bu | Me | s-Bu | 3-Cl—Bn | s-Bu | Me | Me | Bn |
| 55 | Me | Me | Me | s-Bu | 4-Cl—Bn | s-Bu | Me | s-Bu | 4-Cl—Bn | s-Bu | Me | Me | Bn |
| 56 | Propyl | i-Propyl | Me | s-Bu | Bn | s-Bu | Me | s-Bu | Bn | s-Bu | Propyl | i-Pr | Bn |
| 57 | Me | Me | Me | i-Bu | 4-Cl—Bn | i-Bu | Me | i-Bu | 4-Cl—Bn | i-Bu | Me | Me | Bn |
| 58 | Me | Me | Me | i-Bu | 3-Cl—Bn | i-Bu | Me | i-Bu | 3-Cl—Bn | i-Bu | Me | Me | Bn |
| 59 | Me | Me | Me | i-Bu | 2-Cl—Bn | i-Bu | Me | i-Bu | 2-Cl—Bn | i-Bu | Me | Me | Bn |
| 60 | Me | Me | Me | i-Bu | 4-Cl—Bn | i-Bu | Me | i-Bu | Bn | i-Bu | Me | Me | Bn |
| 61 | Me | Me | Me | i-Bu | 3-Cl—Bn | i-Bu | Me | i-Bu | Bn | i-Bu | Me | Me | Bn |
| 62 | Me | Me | Me | i-Bu | 2-Cl—Bn | i-Bu | Me | i-Bu | Bn | i-Bu | Me | Me | Bn |
| 63 | Me | Me | Me | i-Bu | 4-NO$_2$—Bn | i-Bu | Me | i-Bu | 4-NO$_2$—Bn | i-Bu | Me | Me | Bn |
| 64 | Me | Me | Me | i-Bu | 4-NO$_2$—Bn | i-Bu | Me | i-Bu | Bn | i-Bu | Me | Me | Bn |
| 65 | Me | Me | Me | Me | Bn | Me | Me | Me | Bn | Me | Me | Me | Bn |
| 66 | Me | Me | Me | Me | Bn | Me | Me | i-Bu | Bn | i-Bu | M | Me | Bn |
| 67 | Me | Me | Me | Pr | Bn | Pr | Me | Pr | Bn | Pr | Me | Me | Bn |
| 68 | Me | Me | Me | Pr | Bn | Pr | Me | Pr | Bn | i-Bu | Me | Me | Bn |
| 69 | Me | Me | Me | i-Bu | Bn | i-Bu | H | i-Bu | H | i-Bu | Me | Me | Bn |

Me = Methyl
Et = Ethyl
s-Bu = sek.-Butyl
Bn = Benzyl
Pr = Propyl
i-Bu = iso-Butyl
i-Pr = iso-Propyl

5. Preparation of the Compounds of the Formula (IV) According to Process 8

A solution of ethyldiisopropylamine (0.912 mmol) and BOP-Cl (0.438 mmol) was added at 0° C. to a solution of the tetradepsipeptides of the formula (VI) and (V) each (2.52 mmol), in dichloromethane (15 ml). The mixture was subsequently stirred for 1 h at 0° C. and for 1.5 h at room temperature, diluted with 20 ml of dichloromethane, washed twice with a little water, dried over Na$_2$SO$_4$ and concentrated. The residue was purified on silica gel with the eluent cyclohexane-t-BuOMe=2:1.

In accordance with this procedure, compounds of the formula (IV) were obtained in which the substituents have the following meaning:

TABLE 4

| Nr. | $R^1$ | $R^{12}$ | $R^9$ | $R^8$ | $R^7$ | $R^6$ | $R^5$ | $R^4$ | $R^3$ | $R^{10}$ | $R^{11}$ | $R^2$ | A |
|---|---|---|---|---|---|---|---|---|---|---|---|---|---|
| 70 | Et | Et | Me | s-Bu | Bn | s-Bu | Me | s-Bu | Bn | s-Bu | Et | Et | Bn |
| 71 | Propyl | Propyl | Me | s-Bu | Bn | s-Bu | Me | s-Bu | Bn | s-Bu | Propyl | Propyl | Bn |
| 72 | i-Propyl | i-Propyl | Me | s-Bu | Bn | s-Bu | Me | s-Bu | Bn | s-Bu | i-Propyl | i-Propyl | Bn |
| 73 | Me | Me | Me | s-Bu | Bn | s-Bu | Me | s-Bu | Bn | s-Bu | Me | Me | Bn |
| 74 | Me | Me | Me | i-Propyl | Bn | i-Propyl | Me | i-Propyl | Bn | i-Propyl | Me | Me | Bn |
| 75 | Me | Me | Me | Bn | Bn | Bn | Me | Bn | Bn | Bn | Me | Me | Bn |
| 76 | Me | Me | Me | s-Bu | 2-Cl—Bn | s-Bu | Me | s-Bu | 2-Cl—Bn | s-Bu | M | Me | Bn |
| 77 | Me | Me | Me | s-Bu | 3-Cl—Bn | s-Bu | Me | s-Bu | 3-Cl—Bn | s-Bu | Me | Me | Bn |
| 78 | Me | Me | Me | s-Bu | 4-Cl—Bn | s-Bu | Me | s-Bu | 4-Cl—Bn | s-Bu | Me | Me | Bn |
| 79 | Propyl | i-Propyl | Me | s-Bu | Bn | s-Bu | Me | s-Bu | Bn | s-Bu | Propyl | i-Pr | Bn |
| 80 | Me | Me | Me | i-Bu | 4-Cl—Bn | i-Bu | Me | i-Bu | 4-Cl—Bn | i-Bu | Me | Me | Bn |
| 81 | Me | Me | Me | i-Bu | 3-Cl—Bn | i-Bu | Me | i-Bu | 3-Cl—Bn | i-Bu | Me | Me | Bn |
| 82 | Me | Me | Me | i-Bu | 2-Cl—Bn | i-Bu | Me | i-Bu | 2-Cl—Bn | i-Bu | Me | Me | Bn |
| 83 | Me | Me | Me | i-Bu | 4-Cl—Bn | i-Bu | Me | i-Bu | Bn | i-Bu | Me | Me | Bn |
| 84 | Me | Me | Me | i-Bu | 3-Cl—Bn | i-Bu | Me | i-Bu | Bn | i-Bu | Me | Me | Bn |
| 85 | Me | Me | Me | i-Bu | 2-Cl—Bn | i-Bu | Me | i-Bu | Bn | i-Bu | Me | Me | Bn |
| 86 | Me | Me | Me | i-Bu | 4-NO$_2$—Bn | i-Bu | Me | i-Bu | 4-NO$_2$—Bn | i-Bu | Me | Me | Bn |
| 87 | Me | Me | Me | i-Bu | 4-NO$_2$—Bn | i-Bu | Me | i-Bu | Bn | i-Bu | Me | Me | Bn |
| 88 | Me | Me | Me | Me | Bn | Me | Me | Me | Bn | Me | Me | Me | Bn |
| 89 | Me | Me | Me | Me | Bn | Me | Me | i-Bu | 2-Cl—Bn | i-Bu | M | Me | Bn |
| 90 | Me | Me | Me | Pr | Bn | Pr | Me | Pr | 3-Cl—Bn | Pr | Me | Me | Bn |
| 91 | Me | Me | Me | Pr | Bn | Pr | Me | i-Bu | 4-Cl—Bn | i-Bu | Me | Me | Bn |
| 92 | Me | Me | Me | i-Bu | Bn | i-Bu | H | i-Bu | Bn | i-Bu | Me | Me | Bn |

Me = Methyl
Et = Ethyl
s-Bu = sek.-Butyl
Bn = Benzyl
Pr = Propyl
i-Bu = iso-Butyl
i-Pr = iso-Propyl

6. Preparation of the Compounds of the Formula (V) According to Process 11

HCl gas was passed into a solution of the tetradepsipeptide with the formula (VII) (2.848 mmol) in dichloromethane (50 ml) for 2 h at 0° C.

The mixture was subsequently stirred at room temperature for 8 h, concentrated and dried under a high vacuum. The residue was employed without further purification.

In accordance with this procedure, the following compounds of the formula (V) were obtained in which the substituents have the following meaning:

TABLE 5

| Nr. | $R^1$ | $R^{12}$ | $R^9$ | $R^8$ | $R^7$ | $R^{10}$ | A | Z |
|---|---|---|---|---|---|---|---|---|
| 93 | Et | Et | Me | s-Bu | Bn | s-Bu | Bn | OH |
| 94 | Pr | FP | Me | s-Bu | Bn | s-Bu | Bn | OH |
| 95 | i-Pr | i-Pr | Me | s-Bu | Bn | s-Bu | Bn | OH |
| 96 | Me | Me | Me | s-Bu | Bn | s-Bu | Bn | OH |
| 97 | Me | Me | Me | i-Pr | Bn | i-Pr | Bn | OH |
| 98 | Me | Me | Me | Bn | Bn | Bn | Bn | OH |
| 99 | Me | Me | Me | s-Bu | Bn | s-Bu | Bn | OH |
| 100 | Me | Me | Me | i-Bu | 4-Cl—Bn | i-Bu | Bn | OH |
| 101 | Me | Me | Me | i-Bu | 3-Cl—Bn | i-Bu | Bn | OH |
| 102 | Me | Me | Me | i-Bu | 2-Cl—Bn | i-Bu | Bn | OH |
| 103 | Me | Me | Me | i-Bu | 4-NO$_2$—Bn | i-Bu | Bn | OH |
| 104 | Me | Me | Me | Me | Bn | Me | Bn | OH |
| 105 | Me | Me | Me | Pr | Bn | Pr | Bn | OH |
| 106 | Me | Me | Me | i-Bu | H | i-Bu | Bn | OH |

Me = Methyl
Et = Ethyl
s-Bu = sek.-Butyl
Bn = Benzyl
Pr = Propyl
i-Bu = iso-Butyl
i-Pr = iso-Propyl

7. Preparation of the Compounds of the Formula (VI) According to Process 12

A solution of the tetradepsipeptide having the formula (VII) (9.53 mmol) in ethanol (37 ml) was admixed with Pd(OH)$_2$/C (20%) (0.6 g) and hydrogenated for about 3 h at room temperature and atmospheric pressure. The reaction mixture was filtered and concentrated and the residue was separated over silica gel with the eluent t-BuOMe-cyclohexane-ethanol=1:1:0.5.

The following compounds of the formula (VI) in which the subst-tuents have the following meaning were obtained according to this process:

TABLE 6

| Nr. | $R^1$ | $R^{12}$ | $R^9$ | $R^8$ | $R^7$ | $R^{10}$ | D | B |
|---|---|---|---|---|---|---|---|---|
| 107 | Et | Et | M | i-Bu | Bn | i-Bu | H | t-Bu—O— |
| 108 | Pr | Pr | Me | i-Bu | Bn | i-Bu | H | t-Bu—O— |
| 109 | i-Pr | i-Pr | M | i-Bu | Bn | i-Bu | H | t-Bu—O— |
| 110 | Me | Me | M | i-Bu | Bn | i-Bu | H | t-Bu—O— |
| 111 | Me | Me | M | i-Pr | Bn | i-Pr | H | t-Bu—O— |
| 112 | Me | Me | M | Bn | Bn | Bn | H | t-Bu—O— |
| 113 | Me | Me | Me | s-Bu | Bn | s-Bu | H | t-Bu—O— |
| 114 | Me | Me | Me | i-Bu | 4-Cl—Bn | i-Bu | H | t-Bu—O— |
| 115 | Me | Me | Me | i-Bu | 3-Cl—Bn | i-Bu | H | t-Bu—O— |
| 116 | Me | Me | Me | i-Bu | 2-Cl—Bn | i-Bu | H | t-Bu—O— |
| 117 | Me | Me | Me | i-Bu | 4-NO$_2$—Bn | i-Bu | H | t-Bu—O— |
| 118 | Me | Me | Me | Me | Bn | Me | H | t-Bu—O— |
| 119 | Me | Me | Me | Pr | Bn | Pr | H | t-Bu—O— |
| 120 | Me | Me | Me | i-Bu | H | i-Bu | H | t-Bu—O— |

Me = Methyl
Et = Ethyl
s-Bu = sek.-Butyl
Bn = Benzyl
Pr = Propyl
i-Bu = iso-Butyl
i-Pr = iso-Propyl

8. Preparation of the Compounds of the Formula (VII) According to Process 14

Diisopropylethylamine (57.3 mmol) and BOP-Cl (29.8 mmol) were added to a solution, cooled to 0° C., of the didepsipeptide IX (22.9 mmol) and of the didepsipeptide VIII (27.5 mmol) in dichloromethane (80 ml), and the mixture was stirred for 1 h at 0° C. and for 1 h at room temperature. After the precipitate had been filtered off, the solution was diluted with dichloromethane, washed three times with a little water, dried over sodium sulphate and concentrated. The residue was separated on silica gel with the eluent cyclohexane-ethyl acetate=15:1.

In accordance with this procedure, the following compounds of the formula VII were obtained in which the substituents have the following meaning.

TABLE 7

| Nr. | $R^1$ | $R^{12}$ | $R^9$ | $R^8$ | $R^7$ | $R^{10}$ | A | C |
|---|---|---|---|---|---|---|---|---|
| 121 | Et | Et | Me | s-Bu | Bn | s-Bu | H | t-BuO |
| 122 | Pr | Pr | Me | s-Bu | Bn | s-Bu | H | t-BuO |
| 123 | i-Pr | i-Pr | Me | s-Bu | Bn | s-Bu | H | t-BuO |
| 124 | Me | Me | Me | s-Bu | Bn | s-Bu | H | t-BuO |
| 125 | Me | Me | Me | i-Pr | Bn | i-Pr | H | t-BuO |
| 126 | Me | Me | Me | Bu | Bn | Bu | H | t-BuO |
| 127 | Me | Me | Me | s-Bu | Bn | s-Bu | H | t-BuO |
| 128 | Me | Me | Me | i-Bu | 4-Cl—Bn | i-Bu | H | t-BuO |
| 129 | Me | Me | Me | i-Bu | 3-Cl—Bn | i-Bu | H | t-BuO |
| 130 | Me | Me | Me | i-Bu | 2-Cl—Bn | i-Bu | H | t-BuO |
| 131 | Me | Me | Me | i-Bu | 4-NO$_2$—Bn | i-Bu | H | t-BuO |
| 132 | Me | Me | Me | Me | Bn | Me | H | t-BuO |
| 133 | Me | Me | Me | Pr | Bn | Pr | H | t-BuO |
| 134 | Me | Me | Me | i-Bu | H | i-Bu | H | t-BuO |

9. Preparation of the compounds of the formula (VIII) according to Process 17

HCl gas was passed into a solution of the didepsipeptide of the formula (X) (46.0 mmol) in dichloromethane (470 ml) at 0° C. for 2 h. The mixture was subsequently stirred at room temperature for 24 h. The mixture was concentrated and the residue was dried under a high vacuum. The residue was dissolved in water and added dropwise to a suspension of a basic ion exchanger (16.7 g) in 50 ml of water, and the mixture was stirred for 3 h, filtered and concentrated. After drying under a high vacuum, an amorphous powder was obtained which was reacted without further purification.

Analogously to this procedure, the compounds of the formula (VIII) were obtained in which the substituents have the following meaning:

TABLE 8

| Nr. | $R^1$ | $R^9$ | $R^{10}$ | A | Z |
|---|---|---|---|---|---|
| 135 | Et | Me | s-Bu | Bn | OH |
| 136 | Pr | Me | s-Bu | Bn | OH |
| 137 | i-Pr | Me | s-Bu | Bn | OH |
| 138 | Me | Me | s-Bu | Bn | OH |
| 139 | Me | H | i-Bu | Bn | OH |
| 140 | Me | Me | i-Pr | Bn | OH |
| 141 | Me | Me | i-Bn | Bn | OH |
| 142 | Me | Me | Me | Bn | OH |
| 143 | Me | Me | Pr | Bn | OH |

10. Preparation of the compounds of formula (IX) according to Process 18

2.91 g of Pd(OH)$_2$/C (20%) were added to a solution of the didepsipeptide (XI) (60 mmol) in ethanol (163 ml), and the mixture was hydrogenated for about 6 h under atmospheric pressure. After filtering off the catalyst, it was subsequently washed with ethanol, concentrated and dried under a high vacuum. The residue was separated on silica gel with the eluent cyclohexane-ethyl acetate=3:1.

In accordance with this procedure, the compounds of the formula (IX) were obtained in which the substituents have the following meaning:

TABLE 9

| Nr. | $R^{12}$ | $R^8$ | $R^7$ | D | B |
|---|---|---|---|---|---|
| 144 | Et | s-Bu | Bn | H | t-BuO |
| 145 | Propyl | s-Bu | Bn | H | t-BuO |
| 146 | i-Propyl | s-Bu | Bn | H | t-BuO |
| 147 | Me | s-Bu | Bn | H | t-BuO |
| 148 | Me | i-Bu | 4-Cl-Bn | H | t-BuO |
| 149 | Me | i-Bu | 3-Cl-Bn | H | t-BuO |
| 150 | Me | i-Bu | 2-Cl-Bn | H | t-BuO |
| 151 | Me | i-Bu | 4-NO$_2$-Bn | H | t-BuO |
| 152 | Me | i-Pr | Bn | H | t-BuO |
| 153 | Me | Me | Bn | H | t-BuO |
| 154 | Me | Pr | Bn | H | t-BuO |

11. Preparation of the compounds of the formula (X) according to Process 21

The chlorocarboxylic acid XIII (0.212 mol) was added to the caesium salt of aminocarboxylic acid XII (0.212 mol) introduced in 530 ml of dimethyl sulphoxide at room temperature. The mixture was stirred for 20 h at room temperature, poured into saturated sodium chloride solution and extracted four times with ethyl acetate. The combined organic extracts were washed once with a little water, dried over sodium sulphate and concentrated. The residue was purified by column chromatography with the eluent cyclohexane-ethyl acetate=6:1.

In accordance with this procedure, the following compounds of the formula (X) were obtained in which the substituents have the following meaning:

TABLE 10

| Nr. | $R^1$ | $R^9$ | $R^{10}$ | A | B |
|---|---|---|---|---|---|
| 155 | Et | Me | s-Bu | Bn | t-BuO |
| 156 | Propyl | Me | s-Bu | Bn | t-BuO |
| 157 | i-Propyl | Me | s-Bu | Bn | t-BuO |
| 158 | Me | Me | s-Bu | Bn | t-BuO |
| 159 | Me | H | i-Bu | Bn | t-BuO |
| 160 | Me | Me | i-Pr | Bn | t-BuO |
| 161 | Me | Me | Bn | Bn | t-BuO |
| 162 | Me | Me | Me | Bn | t-BuO |
| 163 | Me | Me | Pr | Bn | t-BuO |

12. Preparation of the Compounds of the Formula (XI) According to Process 22

The amino acid of the formula XIV (0.212 mol) was dissolved in 1000 ml of ethanol and 100 ml of water, a 20% strength caesium carbonate solution (200 ml) was added, and the mixture was stirred for 5 h at room temperature. It was then concentrated, codistilled twice with 250 ml of DMF each time, and dried overnight at 80° C. under a high vacuum. 0.212 mol of this caesium salt were initially introduced into 530 ml of dimethyl sulphoxide, 0.212 mol of the chlorocarboxylic acid of the formula XV was added at room temperature, and the mixture was stirred for 20 h at room temperature. The solution was poured into saturated sodium chloride solution, extracted four times with ethyl acetate, and the extracts were dried over sodium sulphate and concentrated. The residue was purified by column chromatography with the eluent cyclohexane-ethyl acetate= 100:1.

In accordance with this procedure the following compounds of the formula (XI) were obtained in which the substituents have the following meaning:

TABLE 11

| Nr. | $R^1$ | $R^9$ | $R^{10}$ | A | B |
|---|---|---|---|---|---|
| 164 | Et | Me | s-Bu | Bn | t-BuO |
| 165 | Propyl | Me | s-Bu | Bn | t-BuO |
| 166 | i-Propyl | Me | s-Bu | Bn | t-BuO |
| 167 | Me | Me | s-Bu | Bn | t-BuO |
| 168 | Me | H | i-Bu | Bn | t-BuO |
| 169 | Me | Me | i-Pr | Bn | t-BuO |
| 170 | Me | Me | Bn | Bn | t-BuO |
| 171 | Me | Me | Me | Bn | t-BuO |
| 172 | Me | Me | Pr | Bn | t-BuO |

We claim:

1. An open-chain octadepsipeptide of the formula (II):

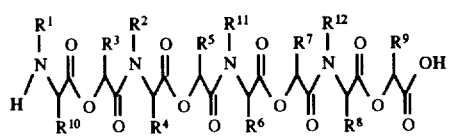

wherein $R^1$ represents $C_{1-8}$-alkyl;

$R^2$ represents $C_{1-8}$-alkyl;

$R^3$ represents hydrogen or aralkyl optionally substituted by halogen or nitro;

$R^4$ represents straight-chain $C_{1-5}$-alkyl, isopropyl, sec-butyl or t-butyl;

$R^5$ represents hydrogen, straight-chain $C_{1-5}$-alkyl or branched $C_{4-7}$-alkyl;

$R^6$ represents straight-chain $C_{1-5}$-alkyl, isopropyl, sec-butyl, t-butyl or aralkyl;

$R^7$ represents aralkyl optionally substituted by halogen or nitro;

$R^8$ represents straight-chain $C_{1-5}$-alkyl, isopropyl, sec-butyl or t-butyl;

$R^9$ represents straight-chain $C_{1-5}$-alkyl or branched $C_{4-7}$-alkyl;

$R^{10}$ represents straight-chain $C_{1-5}$-alkyl, isopropyl, sec-butyl or t-butyl;

$R^{11}$ represents $C_{1-8}$-alkyl; and $R^{12}$ represents $C_{1-8}$-alkyl.

2. A compound of the formula (III):

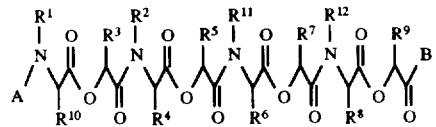

wherein

A represents benzyl;

B represents OH;

$R^1$ represents $C_{1-8}$-alkyl;

$R^2$ represents $C_{1-8}$-alkyl;

$R^3$ represents hydrogen or aralkyl optionally substituted by halogen or nitro;

$R^4$ represents straight-chain $C_{1-5}$-alkyl, isopropyl, sec-butyl or t-butyl;

$R^5$ represents hydrogen, straight-chain $C_{1-5}$-alkyl or branched $C_{4-7}$-alkyl;

$R^6$ represents straight-chain $C_{1-5}$-alkyl, isopropyl, sec-butyl, t-butyl or aralkyl;

$R^7$ represents aralkyl optionally substituted by halogen or nitro;

$R^8$ represents straight-chain $C_{1-5}$-alkyl, isopropyl, sec-butyl or t-butyl;

$R^9$ represents straight-chain $C_{1-5}$-alkyl or branched $C_{4-7}$-alkyl;

$R^{10}$ represents straight-chain $C_{1-5}$-alkyl, isopropyl, sec-butyl or t-butyl;

$R^{11}$ represents $C_{1-8}$-alkyl; and $R^{12}$ represents $C_{1-8}$-alkyl.

3. A compound according to claim 1, of the formula
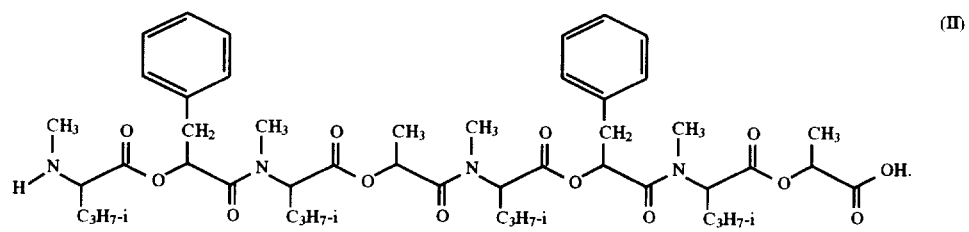
(II)
4. A compound according to claim 1, of the formula
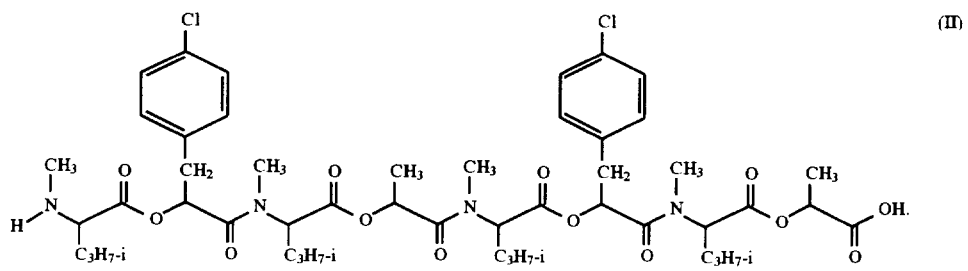
(II)
5. A compound according to claim 1, of the formula
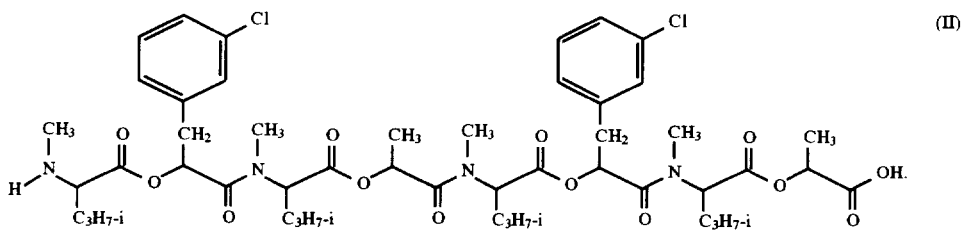
(II)
* * * * *